US010080794B2

(12) United States Patent
Perez et al.

(10) Patent No.: US 10,080,794 B2
(45) Date of Patent: Sep. 25, 2018

(54) SWINE INFLUENZA VIRUSES AND CONSTRUCTS AND USES THEREOF

(71) Applicant: University of Maryland, College Park, MD (US)

(72) Inventors: Daniel R. Perez, Olney, MD (US); Matthew Angel, Bethesda, MD (US)

(73) Assignee: UNIVERSITY OF MARYLAND, COLLEGE PARK, College Park, MD (US)

( * ) Notice: Subject to any disclaimer, the term of this patent is extended or adjusted under 35 U.S.C. 154(b) by 0 days.

(21) Appl. No.: 14/777,450

(22) PCT Filed: Mar. 15, 2014

(86) PCT No.: PCT/US2014/030023
§ 371 (c)(1),
(2) Date: Sep. 15, 2015

(87) PCT Pub. No.: WO2014/145287
PCT Pub. Date: Sep. 18, 2014

(65) Prior Publication Data
US 2016/0030547 A1    Feb. 4, 2016

Related U.S. Application Data

(60) Provisional application No. 61/787,180, filed on Mar. 15, 2013.

(51) Int. Cl.
*A61K 39/145*    (2006.01)
*A61K 39/12*    (2006.01)
*C12N 7/00*    (2006.01)
*C12N 9/12*    (2006.01)
*A61K 39/00*    (2006.01)

(52) U.S. Cl.
CPC ............ *A61K 39/145* (2013.01); *A61K 39/12* (2013.01); *C12N 7/00* (2013.01); *C12N 9/1247* (2013.01); *A61K 2039/5252* (2013.01); *A61K 2039/5254* (2013.01); *A61K 2039/53* (2013.01); *C12N 2760/16034* (2013.01); *C12N 2760/16134* (2013.01); *C12Y 207/07006* (2013.01)

(58) Field of Classification Search
None
See application file for complete search history.

(56) References Cited

U.S. PATENT DOCUMENTS

| 6,171,855 B1* | 1/2001 | Askari | C12N 15/85 435/320.1 |
|---|---|---|---|
| 2008/0026008 A1* | 1/2008 | Tibbs | A61K 39/145 424/209.1 |
| 2008/0050401 A1 | 2/2008 | De Wit et al. | |
| 2009/0324640 A1 | 12/2009 | Kawaoka et al. | |
| 2010/0158939 A1 | 6/2010 | Sambhara et al. | |
| 2010/0285592 A1* | 11/2010 | Curtiss, III | C07K 14/005 435/471 |
| 2012/0207786 A1 | 8/2012 | Smith et al. | |

FOREIGN PATENT DOCUMENTS

WO    WO-2014/145287 A2    9/2014

OTHER PUBLICATIONS

Gorres et al., Clinical and Vaccine Immunology, Nov. 2011, 18(11):1987-1995.*
Heinen et al., Journal of General Virology, 2002, 83:1851-1859.*
Van Reeth and Ma, Current Topics in Microbiology and Immunology, 2013, 370:173-200.*
Yamamoto, M. et al., In Vivo Transfection of Hepatitis C Virus Complementary DNA into Rodent Liver by Asialoglycoprotein Receptor Mediated Gene Delivery. Hepatology. 1995; 22(3):847-55.
Hoffmann, E. et al., "Ambisense" Approach for the Generation of Influenza A Virus: vRNA and mRNA Synthesis from One Template. Virology. 2000; 267:310-7.
Li, L. et al., Development of a Novel Single-Step Reverse Genetics System for the Generation of Classical Swine Fever Virus. Arch Virol. 2016; 161:1831-8.
Ling, X. et al., Cloning and Identification of the Pig Ribosomal Gene Promoter. Gene. 1994; 159(2):375-9.
Mehle, A. et al., Adaptive Strategies of the Influenza Virus Polymerase for Replication in Humans. Proc Natl Acad Sci USA. 2009; 106(50):21312-6.
Moncorgé, O. et al., Investigation of Influenza Virus Polymerase Activity in Pig Cells. J Virology. 2013; 87(1):384-94.
Neumann, G. et al., RNA Polymerase I-Mediated Expression of Influenza Viral RNA Molecules. Virology. 1994; 202:477-9.
Neumann, G. et al., Generation of Influenza A Viruses Entirely from Cloned cDNAs. Proc natl Acad Sci USA. 1999; 96:9345-50.
Qin, Q. et al., Construction of a Transposon-mediated Baculovirus Vector Hanpvid and a New Cell Line for Expressing Barnase. J Biochem Mol Biol. 2005; 38(1):41-8.
Zobel, A. et al., RNA Polymerase I Catalyzed Transcription of Insert Viral cDNA. Nucl Acids Res. 1993; 21(16):3607-14.

(Continued)

*Primary Examiner* — Stacy Brown Chen
(74) *Attorney, Agent, or Firm* — Ballard Spahr LLP

(57) ABSTRACT

Disclosed are compositions and methods comprising vectors and a reverse genetics competent unit comprising one or more recombinant influenza viruses. Recombinant influenza viruses comprising swine RNA polymerase I promoter are disclosed. Constructs comprising swine RNA polymerase I promoter nucleic acid sequences are also provided. Methods of inducing protecting immunity with the recombinant influenza viruses are disclosed. In certain embodiments, the reverse genetics competent unit comprises pathogenic units necessary for producing pathogens de novo from a nucleotide-based vector for influenza virus in swine.

17 Claims, 18 Drawing Sheets
Specification includes a Sequence Listing.

(56) References Cited

OTHER PUBLICATIONS

International Search Report and Written Opinion dated Oct. 10, 2014 by the International Searching Authority for Patent Application No. PCT/US2014/030023, which was filed on Mar. 15, 2014 and published as WO 2014/145287 on Sep. 18, 2014 (Inventor-Perez et al.; Applicant-University of Maryland) (20 pages).

International Preliminary Report on Patentability dated Sep. 15, 2015 by the International Searching Authority for Patent Application No. PCT/US2014/030023, which was filed on Mar. 15, 2014 and published as WO 2014/145287 on Sep. 18, 2014 (Inventor-Perez et al.; Applicant-University of Maryland) (13 pages).

* cited by examiner

SWINE INFLUENZA VIRUSES AND CONSTRUCTS AND USES THEREOF

CROSS-REFERENCE TO RELATED APPLICATIONS

This application is a National Phase Under 35 U.S.C. § 371 of PCT/US2014/030023 filed in the Patent Cooperation Treaty U.S. Receiving Office on Mar. 15, 2014, which claims the benefit of U.S. Provisional Application No. 61/787,180 filed Mar. 15, 2013, the entire contents of which are herein incorporated by reference.

STATEMENT REGARDING FEDERALLY SPONSORED RESEARCH

This invention was made with government support under HHSN266200700010C awarded by the NIH. The government has certain rights in the invention.

REFERENCE TO SEQUENCE LISTING

The sequence listing submitted Sep. 15, 2015 as a text file named "36429_0007U1_Sequence_Listing.txt," created on Sep. 15, 2015, and having a size of 2,113 bytes is hereby incorporated by reference pursuant to 37 C.F.R. § 1.52(e)(5).

FIELD OF THE INVENTION

The disclosed invention is generally in the field of molecular biology and specifically in the area of virology.

BACKGROUND

Swine influenza was first recognized in pigs following the emergence of the 1918 "Spanish Flu" pandemic, and was first isolated in 1930 by Richard Shope (Jour Exp Med 54:373-385 (1931)). This "classical" swine virus (cH1N1) continued to circulate and evolve in pigs until the mid-1990s when a triple reassortant (tr) between a North American avian, a human H3N2, and the cH1N1 was identified (Zhou et al. Jour of Vir 73:8851-8856 (1999)). This new trH3N2 virus quickly reassorted again with the cH1N1's to produce a wide range of subtype constellations (H3N2, H1N1, H1N2, etc.), all with the same triple reassortant, internal gene cassette (TRIG) composed of avian-origin PB2 and PA genes, human-origin PB1, and swine-origin NP, M, and NS genes. The diversity of this virus pool has since been increased with the introduction and establishment of human-origin H1N1 and H1N2 viruses containing the TRIG cassette in US swine populations (Vincent et al. Adv in Virus Res. 72:127-154 (2008)).

The virulence of these viruses varies widely, but infection may result in fever, anorexia, and abortion in pregnant sows resulting in an overall decline in pork production for affected farms. A number of methods have been employed, however, to control this burden. Vaccination and biosecurity have become the most common method to prevent the spread of influenza and to ease the disease burden on the population. Today, inactivated influenza vaccines are commonly available and are designed to match the most common circulating strains. Nevertheless, while these commercial vaccines are available, limited protection is observed in practice due to the antigenic and genetic diversity of influenza viruses circulating in pig population. Furthermore, continued use of these commercial vaccines will most likely result in immune pressure and antigenic divergence of circulating viruses necessitating the reformulation of commercial vaccines. For these reasons, many swine producers have turned to autogenous vaccines to better match strains circulating within their own herds. The use of autogenous influenza vaccines have grown rapidly in recent years due to the diversity of viruses circulating in US pig populations (Vincent et al. Adv in Virus Res. 72:127-154 (2008)). While they are not yet approved for use in swine, live-attenuated influenza vaccines (LAIV) have been shown to provide significant protection to homo- and heterosubtypic challenge in both human and swine models (Loving et al. Journ of Virol 87:9895-9903 (2013)). While both autogenous and LAW could fill an efficacy void left by commercial vaccines, their production still relies heavily on virus growth in eggs or tissue culture systems.

A major drawback in the preparation of LAW and KV vaccines is that production relies on a heavily time-consuming process of growing the viruses in eggs or tissue culture cells. Additionally, since most influenza strains grow poorly in these systems, vaccine strains are produced from reassortants that generally carry the surface gene segments from the candidate virus and other segments from a high growth donor virus. Reverse genetics (RG) has improved the ability to generate such high growth reassortants; however, growing influenza viruses in eggs or tissue culture may result in adaptive changes on the viral surface proteins resulting in antigenic mismatch. LAIV vaccines have an advantage over KV vaccines since they produce broader responses by stimulating both the humoral and the T-cell arms of the immune system. The 2009 pandemic H1N1 virus (pH1N1), however, highlighted the fact that these traditional vaccine production systems are too slow to significantly ameliorate or alter the impact of a pandemic given that the initial pH1N1 vaccine candidates were not well suited for growth in eggs. Alternatively, egg-free influenza vaccine strategies have been investigated including recombinant viral proteins, recombinant viruses, and virus-like particles (VLPs). FLUBLOK™, a baculovirus-based recombinant hemagglutinin influenza vaccine, is the only influenza vaccine approved for human use that does not rely on traditional production systems, but it must also undergo reformulation as a result of antigenic drift. No such vaccines are available for swine.

Type A Influenza (Flu) viruses, also known as influenza A viruses (IAVs), belong to the family Orthomyxoviridae and their genome consists of eight segments of single-stranded RNA of negative polarity (Webby R J, et al. (2007) Cur.r Top. Microbiol. Immunol. 315: 67-83; Yamanaka K, et al. (1991) Proc Natl Acad Sci USA 88:5369-5373; Lopez-Turiso J A, et al. (1990) Virus Res 16: 325-337). The virus has an envelope with a host-derived lipid bilayer and covered with about 500 projecting glycoprotein spikes with hemagglutinating and neuraminidase activities. These activities correspond to the two major surface viral glycoproteins: the hemagglutinin (HA) and neuraminidase (NA), present as homotrimers and homotetramers, respectively. Within the envelope, a matrix protein (M1) and a nucleocapsid (NP) protein protect the viral RNA (Lamb, 1989). The type designation (A, B, or C) is based upon the antigenic features of the M1 and NP proteins. Approximately half of the total genome encodes for the three viral polymerase proteins (segments 1,2 and 3; (Palese et al., 1977). Segment 5 encodes the NP protein. The three-polymerase subunits (PB1, PB2, and PA), the NP and the vRNA are associated in virions and infected cells in the form of viral ribonucleoprotein particles (vRNPs). Segments 4 and 6 encode for the HA and NA genes, respectively. The two smallest segments (7 and 8) encode two genes each with overlapping reading frames, which are generated by splicing of the co-linear mRNA molecules (Lamb and Lai, 1980; Lamb and Lai, 1984; Lamb et al., 1981). In addition to M1, segment 7 encodes for the proton pump transmembrane protein (M2), which has ion channel activity and is embedded in the viral envelope. Segment 8 encodes for NS1, a nonstructural protein that blocks the host's antiviral response, and the nuclear export protein (NS2 or NEP) a structural component of the viral particle. NEP/NS2 interacts with the cellular export machinery and participates in the assembly of virus particles. Recently, NEP/NS2 has also been implicated in playing a role in the regulation of influenza virus transcription and replication. Thus, the eight RNA segments encode for 10-12 viral proteins, including two surface glycoproteins, HA and NA, M2, M1, NS2/NEP, NS1 and, in some influenza viruses (from an alternative translation start site in segment 1) the PB1-F2, an apoptosis modulatory protein [Arias C F, et al. (2009) Arch Med Res 40: 643-654; Zell R, (2006) Emerg Infect Dis 12: 1607-1608; author reply 1608-1609; Chen W, et al. (2001) Nat Med 7:1306-1312.]. Additional viral protein products include PB1-N40, derived from an alternative start site within the PB1 ORF, resulting in a protein product that lacks the first 39 aa of PB1, and PA-X, derived from the PA mRNA and consists of the N-terminal 191 aa of PA fused to 61 aa that result from +1 frameshifting [Jagger B W, et al. (2012) Science 337: 199-204; Yewdell J W, Ince W L (2012) Science 337: 164-165.].

What is needed are methods and compositions for stimulating the immune system of an animal, such as by vaccine methods, wherein the antigenic composition or vaccine, does not need to be manufactured in tissue culture conditions, but instead, the vaccine composition is produced in the subject's body directly. What is needed are compositions and methods of treatment for reduction of infection by vaccination comprising vectors comprising polynucleotides that express pathogenic or oncogenic antigens that stimulate the immune system of a subject to whom the vector is provided. In particular, what is needed are methods and compositions for stimulating the immune system of a pig such that a vaccine composition can be manufactured directly in the pig's body directly.

BRIEF SUMMARY

The present invention comprises methods and compositions for stimulation of the immune system of a subject. The present invention comprises methods and compositions for producing viral antigens, such as influenza virus. An aspect of the present invention comprises vaccination against swine influenza comprising in vivo reverse genetics. Similar to the concept of the "Trojan horse", aspects of the invention comprise providing a vector, such as a baculovirus vector or bacmid, that carry the necessary components for the synthesis of at least a portion of influenza in swine. For example, a vector may comprise nucleic acid sequences that encode and express a live attenuated virus, such as a live attenuated influenza virus (LAIV), in vivo in one or more cells of a pig.

Vectors of the present invention may be delivered by administration methods known to those skilled in the art, including, but not limited to intramuscularly, intranasally, or orally, and may be provided in delivery vehicles including but not limited to, liposomes or cells. For example, provision to a subject of a vector comprising at least a portion of the genome of an influenza virus, results in the generation of live influenza virus in the host along with the stimulation of immune responses against influenza. Methods described herein enable attenuated components of a pathogen to be delivered directly to a host, along with the necessary components for the assembly of those components into a vaccine. Methods disclosed herein bypass the manufacturing step of having to generate a vaccine for a pathogenic organism or oncogenic antigen in an intermediary vehicle such as in vitro culture methods, for example, eggs.

Disclosed are methods and compositions for in vivo delivery of at least a portion of a genome and/or antigenic peptides of influenza comprising a vector and a reverse genetics competent unit of influenza.

Disclosed are methods and compositions for in vivo delivery of influenza virus comprising a vector and a reverse genetics competent unit of influenza, wherein the vector comprises bacmid, baculovirus expression system, synthetic vectors, or vectors known to those skilled in the art; further comprising protein expression units and under the control of appropriate RNA promoters. The cell or host may synthesize and assemble an entire influenza virus from the genome and/or proteins encoded by the vector provided to the cell or host. Additionally, the vaccinated pig receiving the vector may later be challenged by a separate, whole influenza virus to show vaccination protection provided by compositions and methods disclosed herein.

Disclosed are methods and compositions involving recombinant influenza nucleic acid sequences. Disclosed are novel strategies for generating recombinant influenza viruses in swine/porcine cell types. The strategy involves the use of the swine RNA polymerase I (pol I) promoter as a means to transcribe the negative sense RNA species from cloned cDNA required for influenza viral RNA (vRNA) replication, transcription and related applications thereof. Because RNA polymerase I recognizes species-specific promoter sequences, this method is designed to work efficiently in porcine related cell types.

Disclosed are constructs comprising nucleic acid sequences wherein the sequences encode swine RNA polymerase I (pol I) promoter as a means to transcribe the negative sense RNA species from cloned cDNA required for influenza viral RNA (vRNA).

Disclosed are vaccines comprising one or more of the disclosed recombinant viruses. A vaccine of the present invention may comprise a live or killed virus, or may comprise a vaccine composition comprising antigenic or bioactive peptides of one or more recombinant viruses disclosed herein or one or more epitopes antigenic or bioactive peptides of one or more recombinant viruses disclosed herein, or combinations of virus, peptides or epitopes. Vaccine compositions may comprise an adjuvant, such as alum, or immunostimulatory compounds.

Disclosed are recombinant influenza viruses, compositions comprising recombinant influenza viruses, and pharmaceutical compositions comprising recombinant influenza viruses, or antigenic or bioactive peptides of one or more recombinant viruses disclosed herein, or vaccine compositions, or combinations thereof.

A recombinant influenza virus of the present invention may comprise a mutated influenza virus RNA-dependent RNA polymerase. A recombinant influenza virus of the present invention may comprise a genome that encodes for any of the mutations found in the disclosed recombinant proteins. Furthermore, a recombinant influenza virus may comprise any of the disclosed recombinant proteins.

A recombinant influenza virus of the present invention may comprise a rearranged genome. A rearranged genome may have at least eight segments, for example, a rearranged genome may comprise a NS2 nucleic acid sequence removed from segment 8 of the genome. A NS2 nucleic acid sequence may be operably linked to the PB1 gene. A rearranged genome may comprise an exogenous nucleic acid sequence operably linked to a NS1 sequence. A NS1 sequence may comprise a truncated NS1 sequence. An exogenous sequence may be downstream of the truncated NS1 gene. An exogenous sequence may be a H5N1 hemagglutinin (HA) gene.

Recombinant influenza viruses comprising both a swine RNA polymerase I (pol I) and a rearranged genome are disclosed.

Disclosed are methods of immunizing swine against infection by, or reducing the response to infection by, an influenza virus comprising administering an effective amount of one or more of the disclosed recombinant influenza viruses, vaccines or compositions of the present invention. Such methods may comprise administering non-recombinant influenza virus, or wild-type influenza virus and administering one or more recombinant influenza viruses of the present invention. Such administration may be made concurrently or sequentially, and may comprise one or more compositions comprising wild-type and recombinant influenza viruses.

Also disclosed are methods of increasing an antibody response to influenza viral proteins or epitopes comprising administering to a subject an effective amount any of the disclosed recombinant influenza viruses, vaccines or compositions of the present invention.

A recombinant virus of the present invention may be administered in a composition or vaccine.

Disclosed are methods of increasing influenza viral protein production comprising administering to a subject an effective amount of a composition comprising any of the disclosed recombinant influenza viruses, vaccines or compositions of the present invention.

Disclosed herein are methods of increasing influenza viral particle production comprising transfecting cells with a construct comprising a gene that encodes any of the disclosed recombinant proteins in combination with influenza gene sequences, for example, hemagglutinin (HA), neuraminidase (NA), matrix (M1), nucleocapsid (NP), NS1 or NS2. In particular, a recombinant protein may be swine RNA polymerase I (pol I).

Disclosed are methods of inducing a protective immune response against influenza virus infection and disease comprising administering an effective amount of a composition comprising one or more of the disclosed recombinant influenza viruses. In some aspects a recombinant influenza virus is a virus with a swine RNA polymerase I (pol I). In some aspects, a protective immune response may protect against H5N1 and other strains of influenza.

Disclosed are methods of producing an amplicon comprising a) amplifying a first fragment, wherein the first fragment comprises a fragment of a viral nucleic acid sequence and a termination sequence; b) amplifiying a second fragment, wherein the second fragment comprises a fragment of a viral nucleic acid sequence; c) amplifying a third fragment, wherein the third fragment comprises a promoter sequence; and d) combining the three fragments to form an amplicon comprising a termination sequence, a viral nucleic acid sequence, and a promoter sequence. For example, the viral nucleic acid sequence is an influenza viral sequence or swine RNA polymerase I (pol I) as disclosed herein.

Methods of producing an amplicon may have a viral nucleic acid sequence that is an influenza nucleic acid sequence. The influenza nucleic acid sequence may be a hemagglutinin nucleic acid sequence or neuraminidase nucleic acid sequence.

Disclosed herein are methods for plasmid-free influenza replication. Such methods may be used for identifying influenza virus, such in identifying the types of influenza virus found in samples from humans or animals or birds. Plasmid-free methods are faster than methods comprising steps for cloning or plasmid production. Plasmid-free methods may overcome plasmid methods where particular proteins, such as HA or N, may be difficult to clone or the clone reproduces at a low or poor level.

Disclosed are influenza viruses identified or produced by a method comprising transfecting cells with one or more amplicons produced by methods disclosed herein along with the remaining influenza nucleic acid segments required to produce an influenza virus. The remaining influenza nucleic acid segments may be present on plasmids or not. The remaining influenza nucleic acid segments may be from a different strain of influenza or the same influenza strain compared to the influenza gene or genes present on one or more amplicons. In an aspect, at least one other gene required for producing influenza virus may be present on an amplicon. An amplicon may have a swine RNA polymerase I (pol I) sequence. An amplicon may have a hemagglutinin sequence. An amplicon may have a neuraminidase sequence. The remaining influenza nucleic acid segments required to produce influenza virus may be chosen from the known influenza proteins, including, but not limited to, hemagglutinin, neuraminidase, matrix, nucleocapsid, PB1, PB2, PA, NS1, or NS2.

Also disclosed are combinations of disclosed recombinant viruses and constructs and methods of the using these combinations. For example, disclosed are recombinant influenza viruses having a swine RNA polymerase I (pol I) sequence.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

cells were transfected with 1 µg pPIG-GLuc (NS) together with 1 µg of each plasmid expressing IAV PB2, PA, and NP. As a control for IAV amplification, transfections were done with or without the addition of PB1. Luciferase values represent fold change mock. p values<0.001 at each time point.

Figure 3:
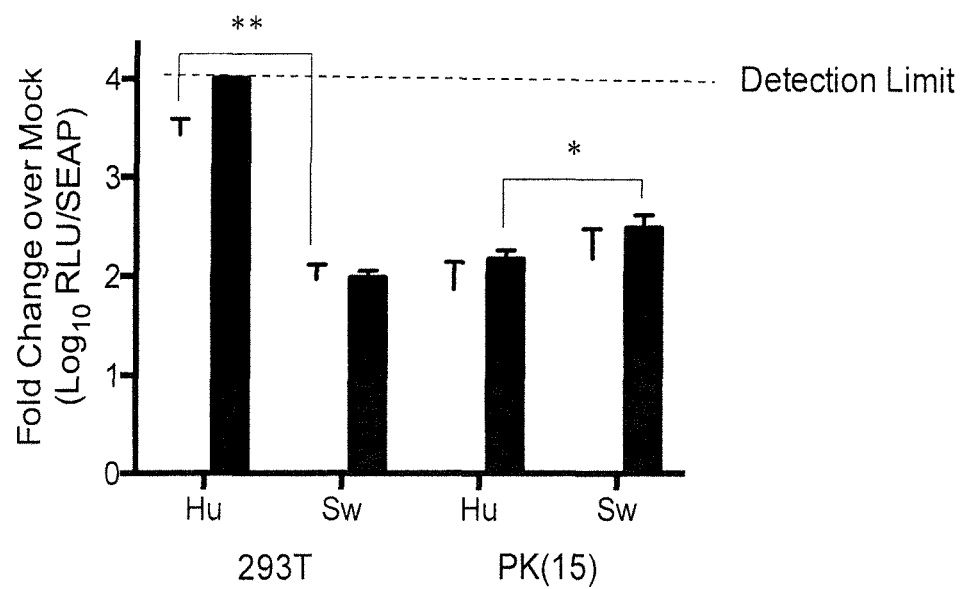

FIG. 3: RNA Polymerase I activity in human and swine cell types. HEK293T or PK(15) cells were transfected with influenza-amplifiable GLuc vRNA reporter genes expressed from either a human (Hu) or Swine (Sw) RNA polymerase I promoter. The viral replication complex was reconstituted with PB2, PB1, PA, and NP expressed from pcDNA3.1 vectors. Luciferase activity was assayed at 24 (white) and 48 (black) hours post transfection. All transfections normalized to SEAP.

Figure 4:
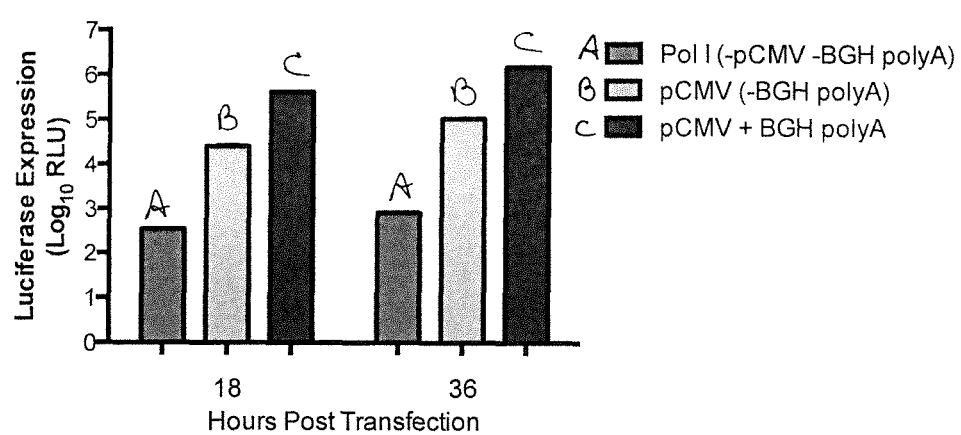

FIG. 4: Contributions of the CMV early promoter and BGH polyadenylation signal to reporter expression. PK(15) cells were transfected with either the pPIGv-GLuc (NS) reporter containing only the RNA polymerase I promoter (red), an intermediate plasmid encoding both the RNA pol I and pCMV promoters (orange), or pPIG-GLuc (NS) containing the RNA polI, pCMV, and the BGH polyadenylation signal (blue). All results are normalized to background.

Figure 5:
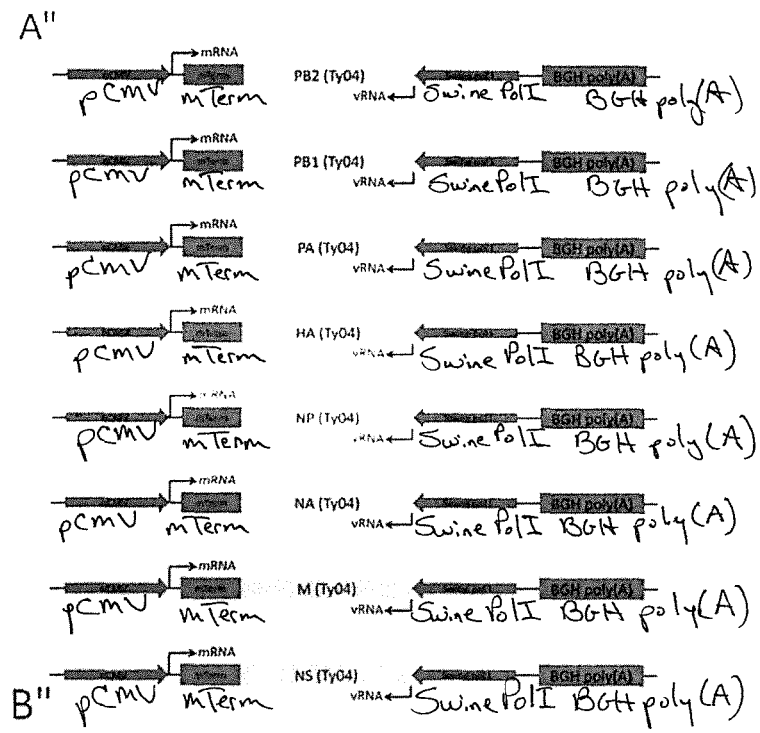
Figure 5:
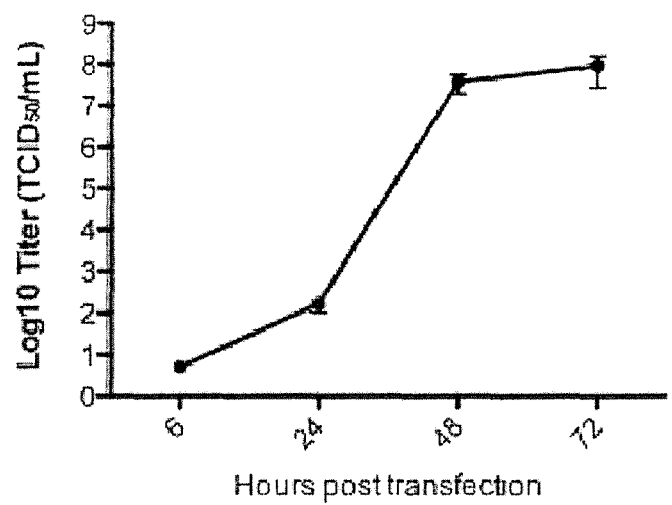

FIG. 5: Swine based influenza reverse genetics. A) Schematic diagram of eight segments from A/turkey/Ohio/313053/2004 (trH3N2) cloned into pPig2012 swine reverse genetics vector. B) Rescue of the eight plasmids in PK(15)/MDCK co-culture (n=3).

Figure 6:
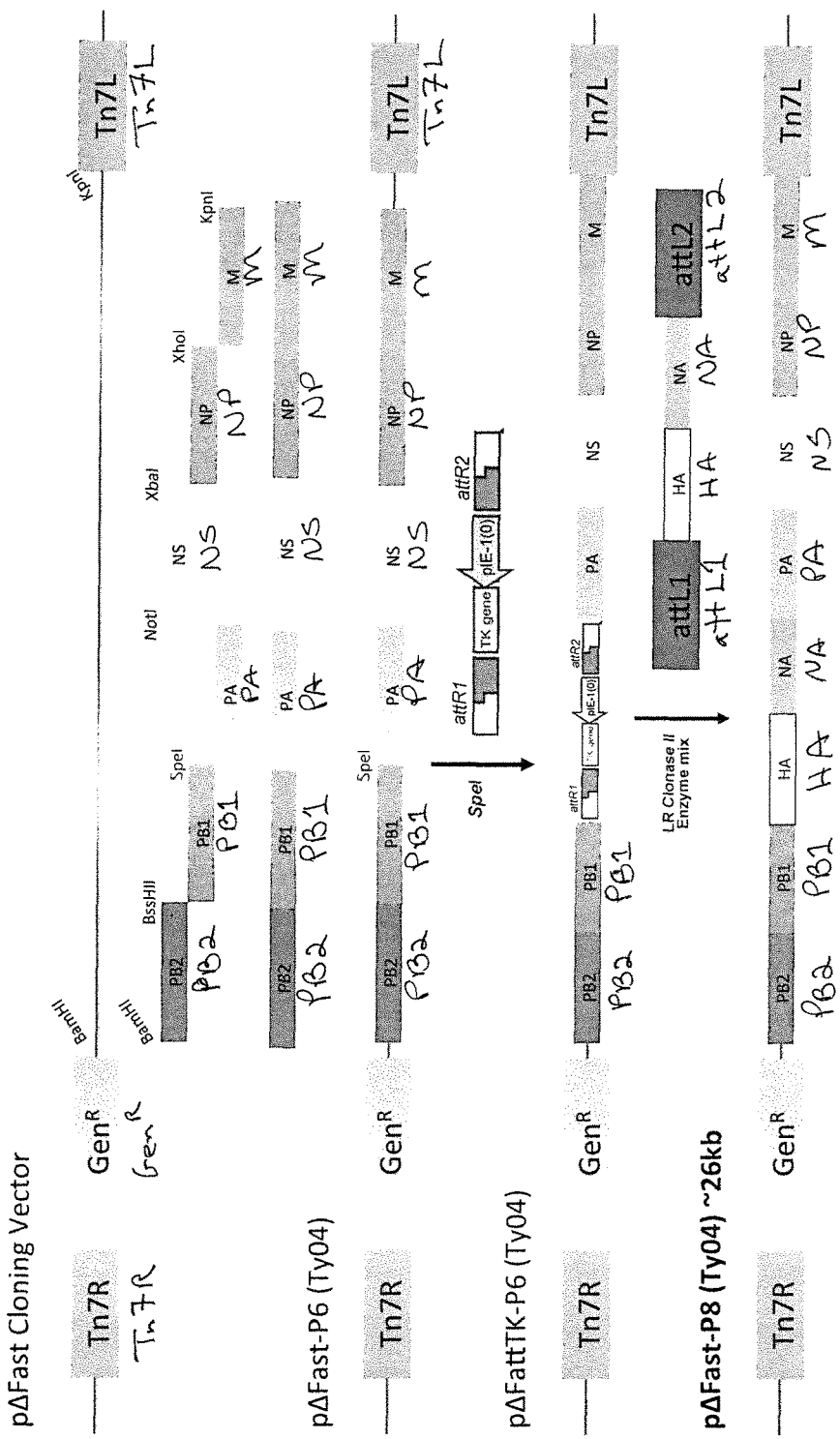

FIG. 6: Strategy for consolidating the reverse genetic cassettes for Ty04 into pΔFast.

Figure 7:
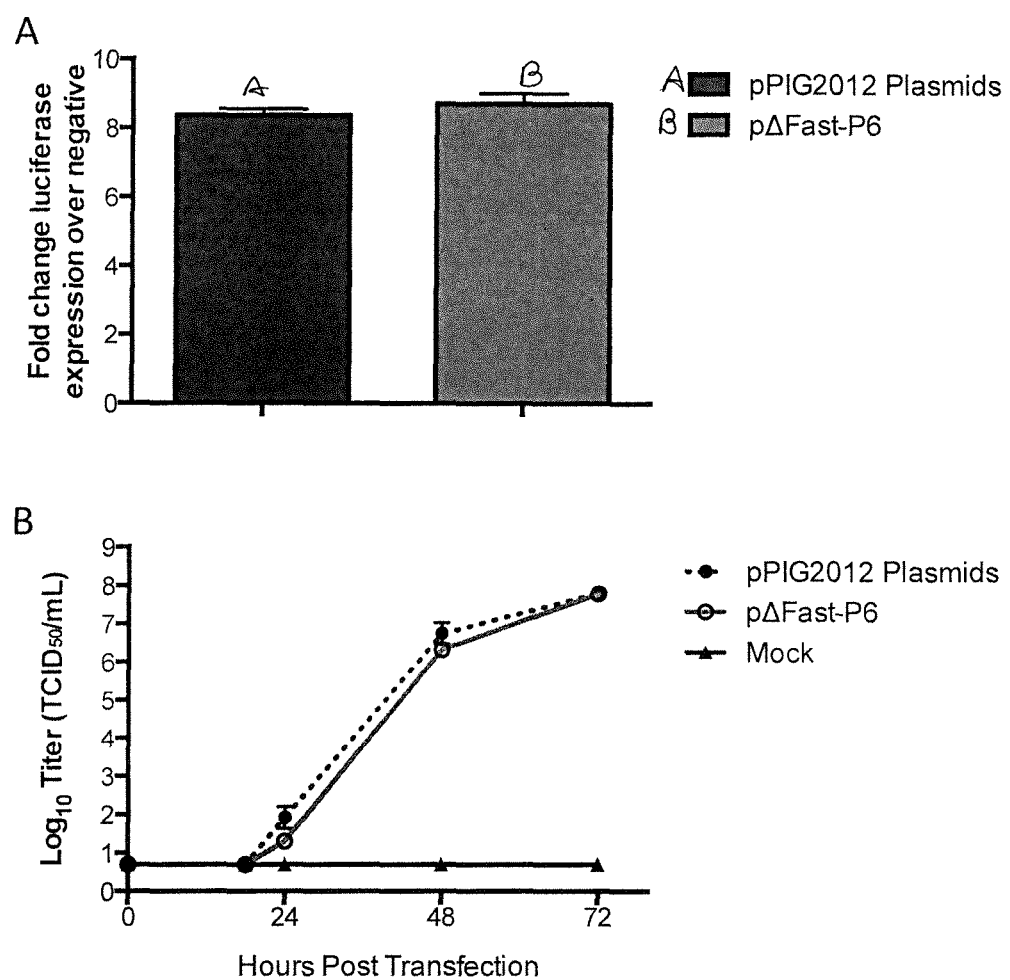

FIG. 7: Characterization of pΔFast-P6 (Ty04) backbone vector. A) PK(15) cells were transfected with either 6 µg pΔFast-P6 (Ty04) or the copy number equivalent genes in pPIG2012. At 24 hpt, supernatant was harvested and assayed for luciferase activity (N=2). B) Virus rescue of 6 µg pΔFast-P6 (Ty04) or equivalent genes in pPIG2012 complemented with pPIG-HA and pPIG-NA in PK(15)/MDCK co-culture (4:1 ratio, N=3). Aliquots from 4 time points were titrated by $TCID_{50}$ in MDCK cells.

Figure 8:
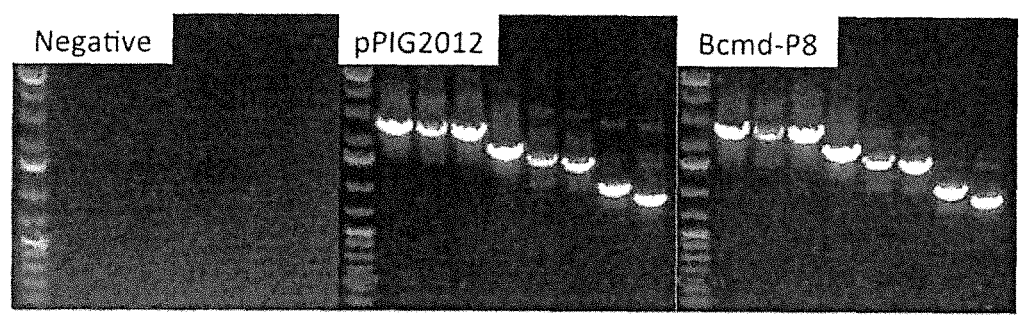

FIG. 8: Amplification of the influenza genome from Bcmd-P8. Each of the eight genes from A/turkey/Ohio/313053/2004 (trH3N2) were amplified with universal primers and separated on a 0.75% agarose gel. The negative panel shows the results of PCR without template. Initial lane in each panel contains 1 kb Plus DNA latter.

Figure 9:
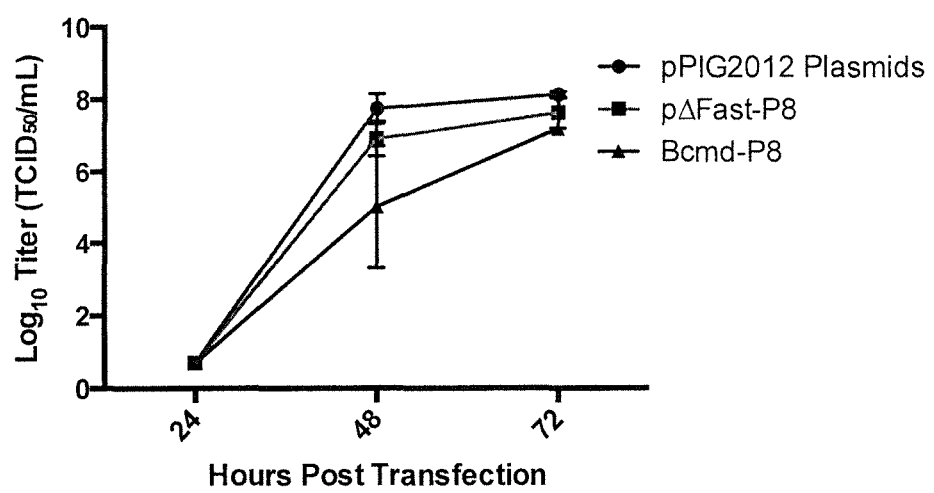

FIG. 9: Rescue kinetics of complete reverse genetic constructs. 293T/MDCK co-cultures were transfected with either eight pPIG2012 plasmids (blue), a single pΔFast plasmid encoding all eight influenza gene cassettes (red), or a bacmid containing all eight influenza gene cassettes (black) from Ty04 under the control of the swine polymerase I promoter vector (N=3). Copy numbers of plasmids (each gene) and bacmids were normalized to the amount of pPIG-PB2 in 1 µg.

Figure 10:
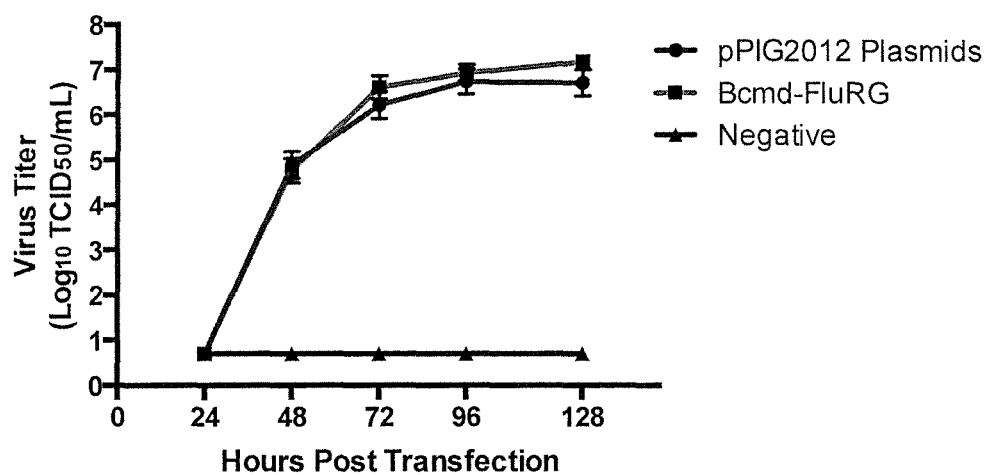

FIG. 10: Low copy rescue of influenza virus. Bacmid or eight pPIG2012 plasmids were transfected into 293T/MDCK co-culture at 2.78×1010 copies of either the bacmid or each plasmid. Supernatant was harvested every 24 hours for 128 hours and titrated on MDCK. N=3.

Figure 11:
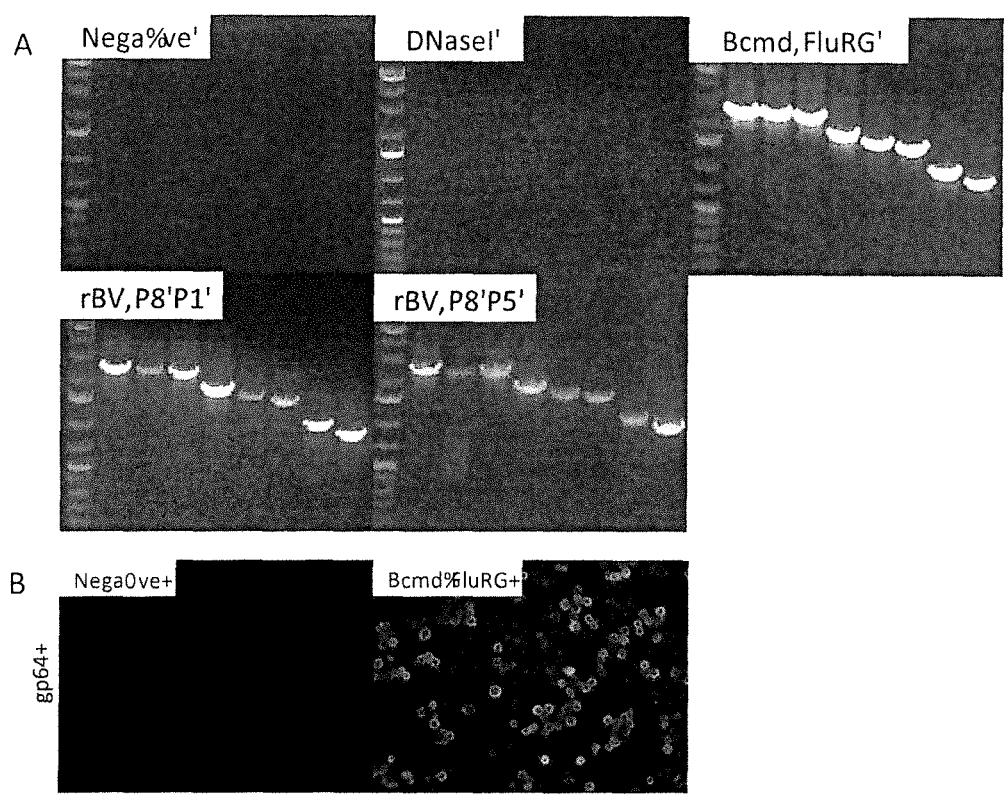

FIG. 11: Rescue of rBV-P8 baculovirus encoding influenza reverse genetic cassettes. A) PCR amplification of baculovirus vectored influenza reverse genetic cassettes using full length, gene specific primers. B) Immunofluorescent staining of baculovirus gp64 on the surface of insect Sf9 cells.

Figure 12:
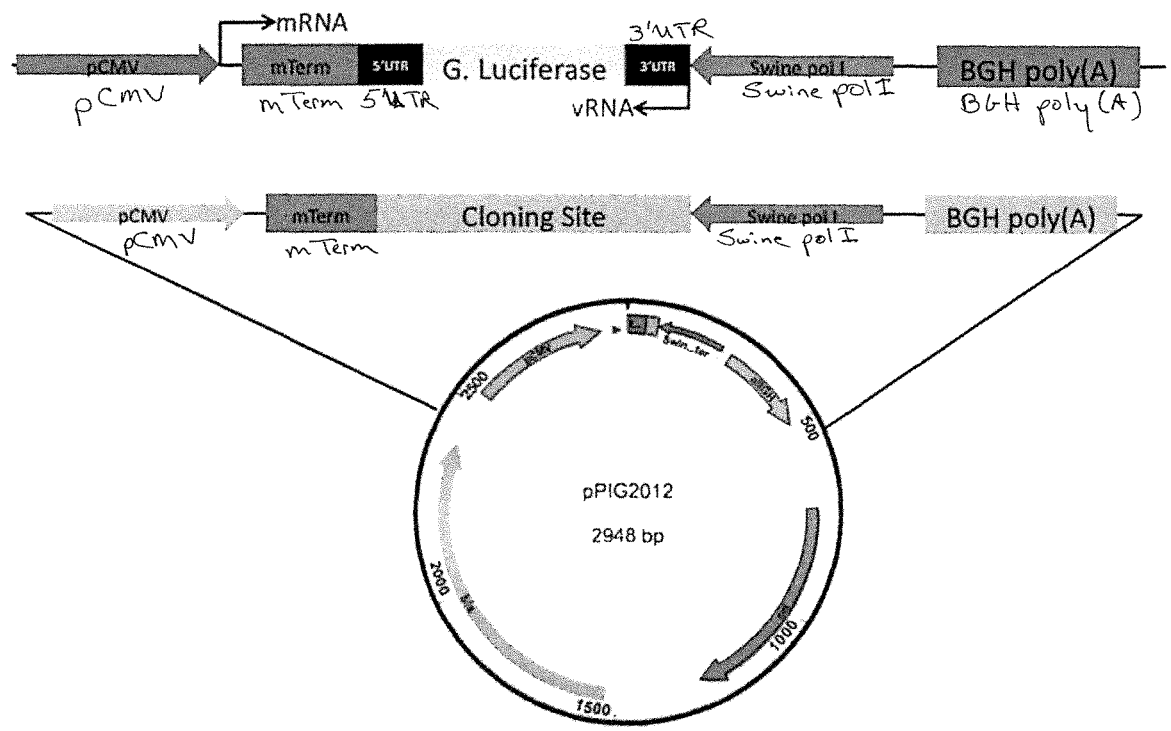

FIG. 12 provides a schematic showing a bidirectional reverse genetic vector with the addition of an RNA polymerase II promoter to transcribe the mRNA of the same gene.

Figure 13:
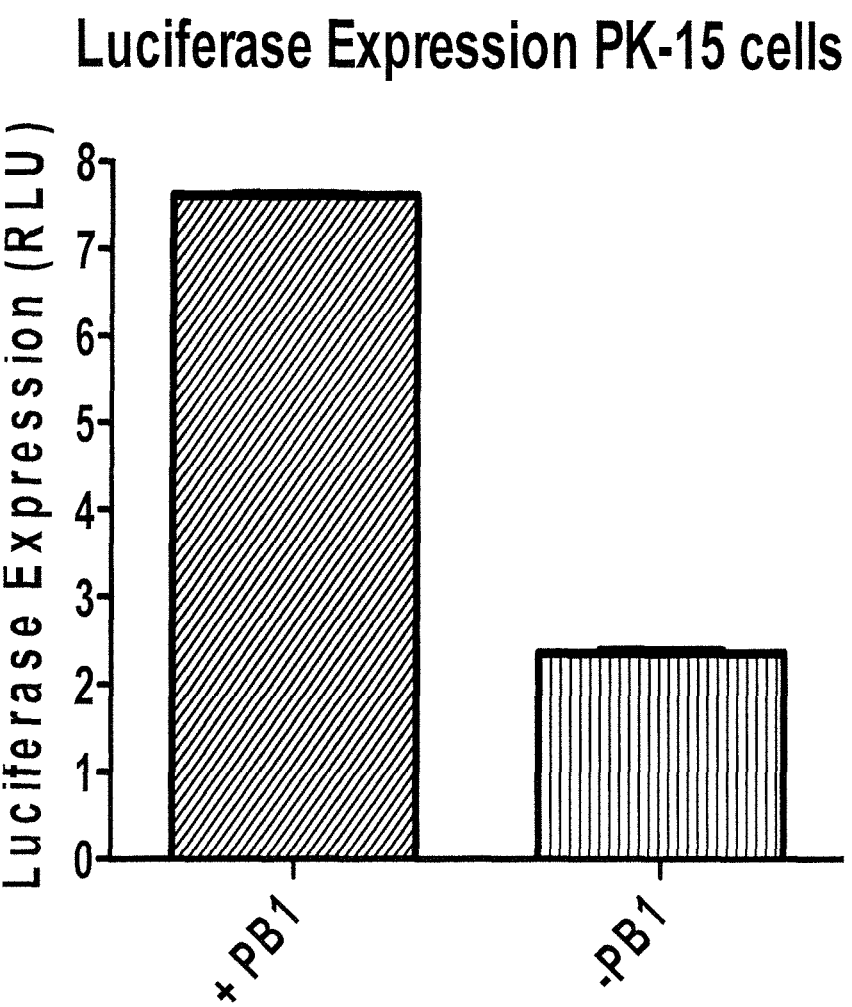

FIG. 13 provides a graph showing luciferase expression in PK-15 cells.

Figure 14:
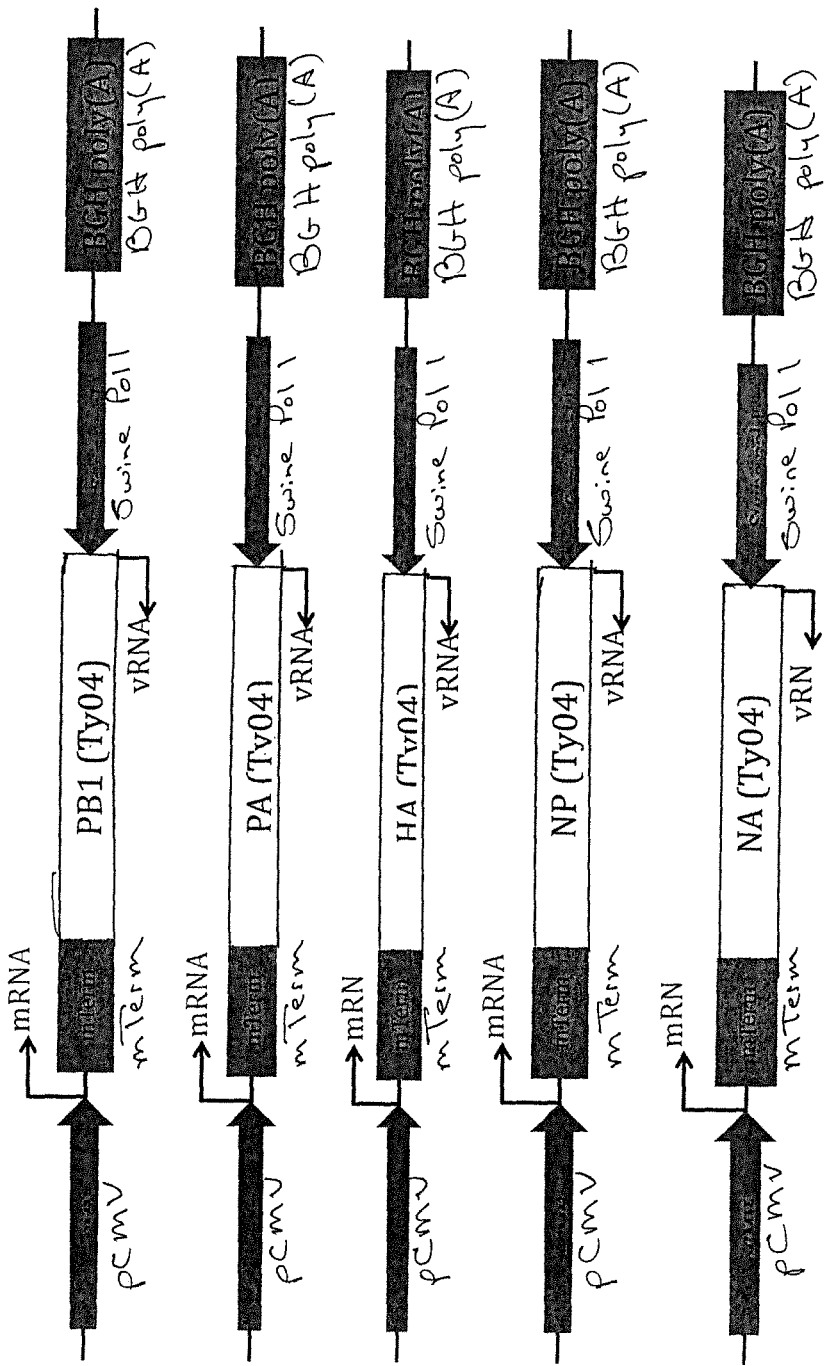

FIG. 14 provides a schematic showing cloned influenza cDNAs

Figure 15:
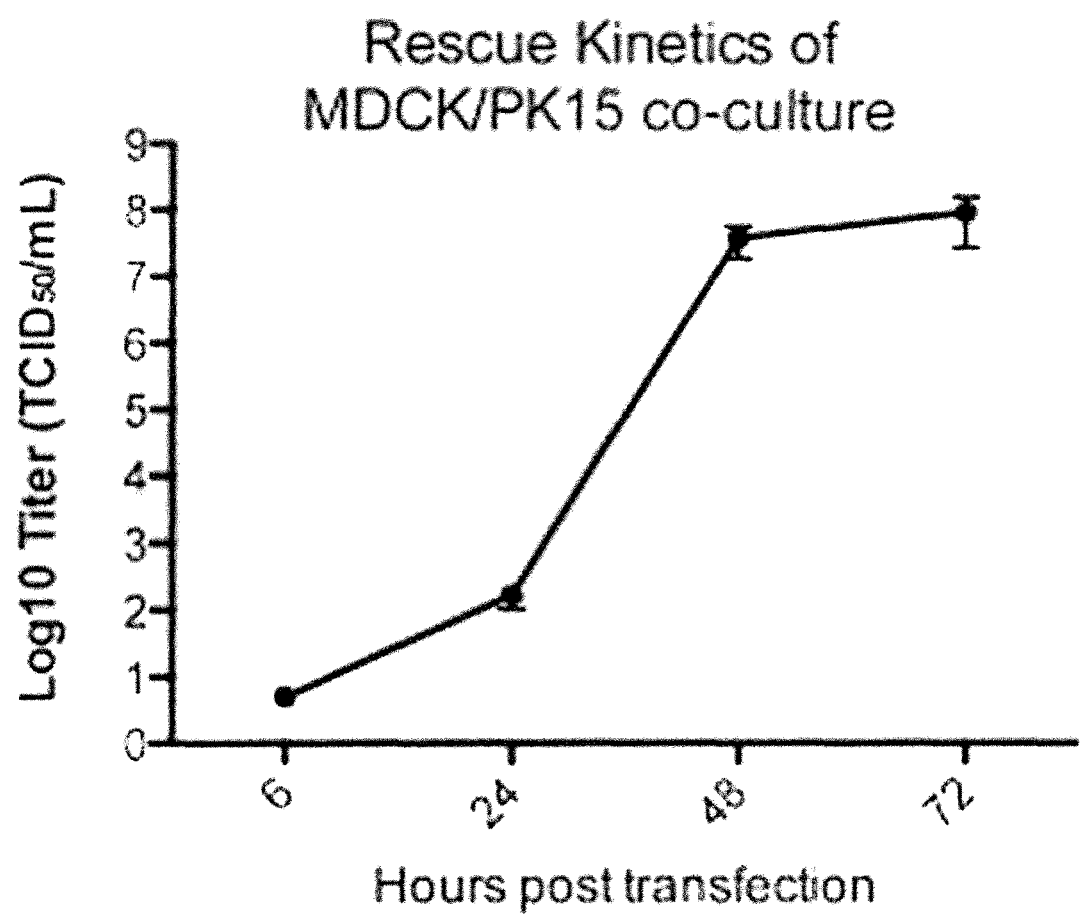

FIG. 15 provides constructs for the rescue kinetics of MDCK/PK-15 coculture.

Figure 16:
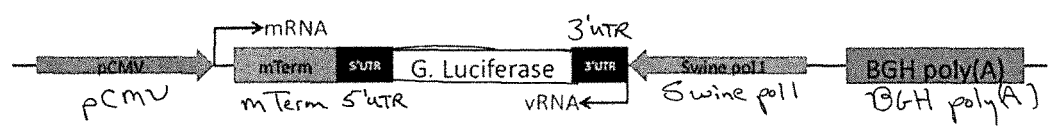

FIG. 16 provides a schematic for a reporter.

Figure 17:
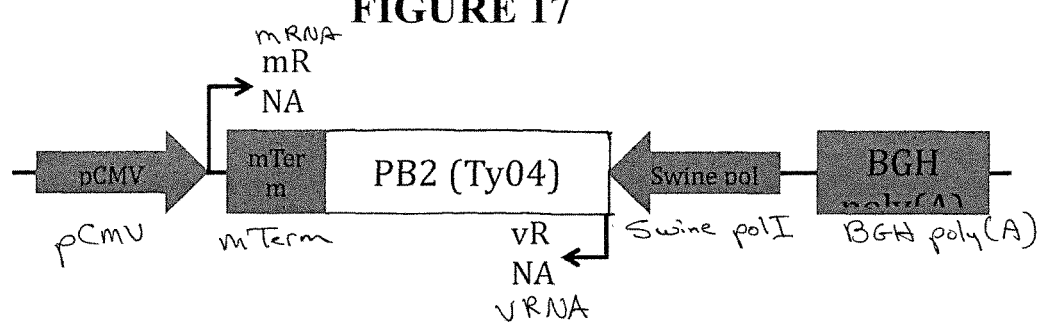
Figure 17:
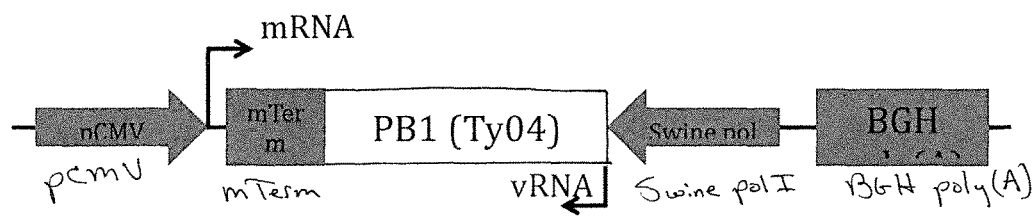

FIG. 17 provides a graph showing cloned influenza cDNAs.

Figure 18:
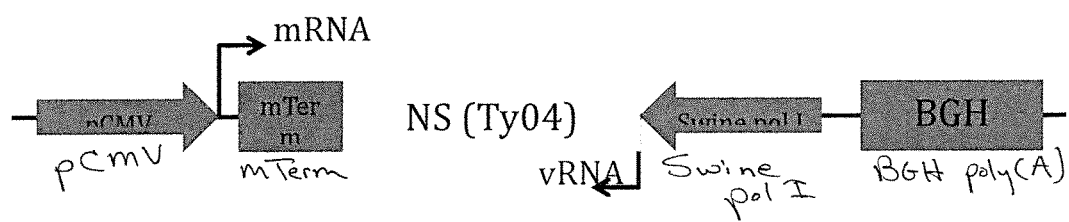

FIG. 18 provides a construct.

DETAILED DESCRIPTION

The disclosed method and compositions can be understood more readily by reference to the following detailed description of particular embodiments and the Example included therein and to the Figures and their previous and following description.

The present invention comprises compositions and methods for stimulating the immune system of a pig, by providing compositions comprising DNA constructs that express one or more desired antigens, such as pathogenic antigens including but not limited to viruses such as influenza virus, in the pig to stimulate an immune response by the pig. Methods and compositions disclosed herein comprise providing DNA constructs that express nucleic acid polymers that may, for example, be the genome or a portion of a genome of an influenza virus. Such a polynucleotide molecule may be a template for protein synthesis. Methods and compositions disclosed herein may be used for manipulating pathogenic agents or portions of pathogens to provide better vaccines, increased pathogenic protein or genome expression, and/or for producing pathogenic agent-containing vectors. The present invention provides compositions and methods for manipulating influenza virus or portions of the influenza virus to provide in vivo vaccines in pigs.

Evidence suggests that swine play a major role in the adaptation of influenza viruses from the avian reservoir into the human population. This is indeed the case in the most recent pandemic in which viruses from the classical swine H1N1, 1967-derived H3N2 human, and North American avian lineages converged in swine to produce the 2009 swine-origin pandemic virus. It is therefore reasonable to assert that swine health and human health are intimately intertwined, and that protection of swine heard from influenza viruses may have a direct influence on emerging pandemic viruses in humans. While biosecurity and vaccination provide the best means of protection in production facilities, a high degree of antigenic diversity within currently circulating and emerging strains complicate vaccination efforts. Vaccines must be produced quickly and reliably without changing the antigenicity of the seed strain. Although the advent of reverse-genetics for influenza virus has enabled vaccines to be produced much more quickly, seed stocks must ultimately be propagated in traditional substrates such as tissue culture or embryonated eggs. Vaccine candidate viruses also may not be well adapted for growth in these non-natural substrates, as was the case for the 2009 human H1N1 vaccine, and adapting for high growth strains may adversely affect the intended antigenicity of the vaccine stock. Despite the experience with traditional vaccine production and access to more recent technology, vaccination of animals and humans during the 2009 pandemic did little to significantly ameliorate the impact of the pandemic. Next generation vaccines must be able to be produced rapidly, in high yields, and with high antigenic fidelity to the circulating strains.

Despite some shortcomings, vaccination remains the first line of defense against many pathogenic infections, especially influenza infections, yet vaccine production methods are slow, antiquated, and expensive to effectively reduce the infectious agent's burden during epidemic or pandemic periods. There is a great need for alternative vaccines and vaccination methods with a global scale impact. The methods and compositions described herein provide a novel approach for generating effective vaccines against infectious agents, including, but not limited to influenza infections. The methods described herein enable the generation of in vivo virus production, i.e. in vivo influenza virus production. Though influenza is provided as an example herein, the present invention contemplates that pathogenic agents other than influenza are comprised in the methods and compositions disclosed herein, and the invention is not to be limited by the disclosure herein. Those of skill in the art could perform the methods and compositions taught herein with such an understanding.

DNA vaccines are undoubtedly the most cost-effective vaccines to produce. Despite their simplicity and solid safety history, DNA vaccination development has been hampered by its low immunogenicity in humans (Gurunathan et al. Ann. Rev. Immunol. 18:927-974 (2000)). The inventors herein overcame the limitation in immunogenicity of DNA vaccines by providing alternative machinery capable of amplifying the antigen of interest. The present invention enables the teaching of DNA vaccine development with enhanced antigen production in vivo.

In certain embodiments, the present invention comprises a vector comprising a reverse genetics competent unit. The vector may comprise any vector known to those skilled in the art, including but not limited to baculovirus expression vectors, bacmids, vaccinia virus, other large viruses, and synthetic vectors. A "reverse genetics competent unit" comprises portions of a pathogenic agent for synthesis of entire pathogens de novo or antigenic portions of a pathogenic agent from a nucleotide-based vector. In certain embodiments, the reverse genetics competent unit comprises portions of a pathogenic agent necessary for producing pathogens de novo from a nucleotide-based vector for infectious agents including but not limited to, influenza virus, poliovirus, Newcastle disease virus, and other agents such as those comprising positive sense and negative sense RNA viruses, bacterial pathogens and parasitic pathogens. Vectors of the present invention may encode at least a portion of genomes, proteins or peptides, that when expressed by the vector and or cell lead to the synthesis of an entire pathogen, or provide antigens to which a subject, such as a pig, having an immune system may respond. The immune response may provide modulation of the immune response in the subject when the subject is subsequently challenged with the pathogen. A vector may comprise at least a portion of an antigen to which a subject having an immune system may respond. The immune response may provide modulation of the immune response in the subject when the subject is exposed to the oncogenic protein.

Baculoviruses (BVs) are powerful transducers of mammalian and avian cells. BVs have been approved by the FDA and are currently being evaluated for gene therapy in the treatment of cancer and other genetic diseases. Aspects of the present invention provide a new method for influenza vaccination that relies on the concept of in vivo reverse genetics, which is the concept of a "Trojan horse" approach in which a vector, such as a baculovirus vector, carries the necessary components for the generation of a live attenuated influenza virus (LAIV) in vivo.

The present invention provides DNA or a baculovirus-based vaccine for the production of influenza viruses in swine cells with the ability to produce an in vivo reverse genetic vaccine. As detailed in the Examples, cloned cDNA from a triple reassortant swine virus, Ty04, was introduced into a reverse genetic vector and transcribed into a viral-like RNA species under the control of a porcine RNA polymerase I promoter. The reverse genetic cassettes for each of the eight segments, consisting of the RNA polymerase II promoter, the cloned cDNA segment, the porcine RNA polymerase I promoter, and the bovine growth hormone polyadenylation signal, were serially cloned into a single shuttle vector and transposed into a bacmid encoding the AcNPV genome. The results discussed in the Examples demonstrate that bacmid is capable of rescuing both influenza and baculovirus in mammalian and insect cell culture, respectively. Consequently, the present invention provides for the first time a novel methodology for vaccine production in swine comprising the delivery of a reverse genetics competent unit for swine influenza specifically including swine/porcine RNA polymerase I promoter.

Although single plasmid rescue strategies have been used in the prior art these large plasmids with repetitive promoter sequences are unstable in *E. coli*, and the cassettes are often lost. In contrast, the bacterial artificial chromosomes (BACs), such as bMON14272 used here, are based off of the F factor and are maintained at low copy numbers thus increasing the stability of the DNA. Furthermore, the present invention allows for the rapid exchange of surface antigens by using the Gateway cloning system, and doesn't require ligations into large vectors. Given the higher cloning capacity of the BAC compared to traditional plasmids, in certain embodiments, the present invention further comprises additional genes to act as immune modulators, increasing the response to the rescued virus. Accordingly, the present invention provides a reverse genetic system tailored to the rescue of influenza virus in swine cells with the potential to act as DNA or baculovirus based vectors for in vivo virus rescue and vaccination.

The present inventions comprises methods and compositions for influenza, for example, swine influenza. A method comprises a method for generating recombinant influenza viruses in swine comprising administering a genetic construct wherein the construct comprises swine RNA polymerase. A method comprises wherein the swine RNA polymerase promoter comprises the sequence of SEQ ID NO: 1. A method comprises wherein the swine RNA polymerase transcribes negative sense RNA species from cloned cDNA required for influenza viral RNA replication. A method comprises wherein the construct further comprises genes that encode hemagglutinin, neuraminidase, matrix, nucleocapsid, PB1, PB2, PA, NS1 or NS2. A method wherein the construct comprises a reverse genetic vector transcribed into a viral-like RNA species, wherein the reverse genetic vector comprises genetic cassettes for RNA polymerase II promoter, cloned cDNA segment, porcine RNA polymerase I promoter, and bovine growth hormone polyadenylation signal. A method comprises wherein the reverse genetic vector is serially cloned into a single shuttle vector and transposed into a bacmid. A method comprises wherein the reverse genetic vector is serially cloned into a single shuttle vector and transposed into a baculovirus expression system. A method comprises wherein the RNA polymerase II promoter comprises a CMV promoter. A method comprises wherein the reverse genetic vector further comprises a murine polymerase I terminator sequence. A method comprises wherein administering the genetic construct results in immunity against influenza.

Compositions of the present invention comprise compositions of genetic constructs. A composition comprises a genetic construct wherein the construct comprises swine RNA polymerase and cloned cDNA required for influenza viral RNA replication. A composition comprises wherein the swine RNA polymerase comprises the sequence of SEQ ID NO:1. A composition comprises wherein the construct further comprises genes that encode hemagglutinin, neuraminidase, matrix, nucleocapsid, PB1, PB2, PA, NS1 or NS2. A composition comprises wherein the construct comprises a reverse genetic vector transcribed into a viral-like RNA species, wherein the reverse genetic vector comprises genetic cassettes for RNA polymerase II promoter, cloned cDNA segment, porcine RNA polymerase I promoter, and bovine growth hormone polyadenylation signal. A composition comprises wherein the reverse genetic vector is serially cloned into a single shuttle vector and transposed into a bacmid. A composition comprises wherein the reverse genetic vector is serially cloned into a single shuttle vector and transposed into a baculovirus expression system. A composition comprises wherein the RNA polymerase II promoter comprises a CMV promoter. A composition comprises wherein the reverse genetic vector further comprises a murine polymerase I terminator sequence. wherein administering the genetic construct results in immunity against influenza. A compositions disclosed herein may be provided as pharmaceutical composition. A composition comprises a pharmaceutical carrier.

The present invention comprises methods of in vivo vaccine synthesis. A method comprises a method of in vivo synthesis of a swine influenza vaccine, comprising, providing to at least one cell of a pig a vector comprising an exogenous DNA construct encoding at least a portion of an influenza virus, wherein one or more antigenic peptides encoded by the DNA construct are expressed in the cell and stimulate an immune response in the subject to the pathogenic agent and wherein the DNA construct comprises swine RNA polymerase I promoter. A method comprises wherein one or more copies of at least a portion of a genome of the influenza virus are expressed in the cell. A method comprises wherein the DNA construct is a reverse genetics competent unit. A method comprises wherein multiple copies of the genome are expressed in the cell. A method comprises wherein the vector further comprises a reverse genetics competent unit. A method comprises wherein the vector comprises a bacmid, a baculovirus expression system, or a synthetic vector. A method comprises wherein the vector comprises a recombinant baculovirus vector and a reverse genetics competent unit comprising influenza virus. A method comprises wherein the vector comprises a bacmid and a reverse genetics competent unit of influenza A virus. A method comprises wherein the vector comprises protein expression units and genome transcription units under the control of appropriate promoters. A method comprises protein expression units under the control of RNA pol II promoters and viral transcription units under the control of RNA pol I promoters. A method comprises wherein live attenuated influenza vaccine is produced directly in vivo. A method comprises providing the vector in a cell to the swine or pig, terms which may be used interchangeably. A method comprises wherein two vectors are provided, and one vector encodes surface antigens of the influenza virus. A method comprises wherein two vectors are provided, and one vector encodes proteins used in replication of the influenza virus.

The present invention comprises vaccine compositions. A composition an influenza vaccine composition, comprising a bacmid vector comprising a reverse genetics competent unit of influenza virus, wherein the genome of influenza virus is expressed is a cell and one or more antigenic peptides of influenza are expressed in a cell and wherein the reverse genetics competent unit further comprises swine RNA polymerase I promoter. A composition disclosed herein may be provided as a pharmaceutical composition. A composition comprises wherein the composition is a pharmaceutical composition. A composition transducer enhancers or adjuvants. A composition comprises wherein the composition is formulated to be administered via intranasal inoculation, intradermal inoculation, microneedle administration, subcutaneous administration, aerosol delivery, or intramuscular administration. A composition comprises wherein the reverse genetics competent unit of influenza virus comprises PB2, PB1, PA, NP, M, and NS gene segments. A composition comprises wherein the gene segments are from the influenza virus strain A/Puerto Rico/8/1934 (H1N1). A composition comprises wherein the bacmid vector of the composition is the result of recombination between a bacmid vector encoding internal proteins of influenza and a bacmid vector comprising the HA and N proteins of influenza so that the bacmid vector of the composition encodes and expresses each of the proteins of influenza.

The present invention comprises methods for immune modulation, wherein modulation may be stimulating or inhibiting. A method comprises a method of immune stimulus from in vivo synthesis of a vaccine, comprising, providing to at least one cell of a subject at least one vector comprising an exogenous DNA construct encoding at least a portion of an influenza virus, wherein one or more antigenic peptides encoded by the DNA construct are expressed in the cell and stimulate an immune response in the subject to the pathogenic agent and wherein the DNA construct comprises swine RNA polymerase I promoter. A method comprises wherein one or more copies of a portion of a genome of the influenza virus are expressed in the cell. A method comprises wherein the DNA construct is a reverse genetics competent unit. A method comprises wherein multiple copies of the genome are expressed in the cell. A method comprises wherein the vector further comprises a reverse genetics competent unit. A method wherein the vector comprises a bacmid, a baculovirus expression system, or a synthetic vector. A method comprises wherein the vector comprises a recombinant baculovirus vector and a reverse genetics competent unit comprising influenza virus. A method comprises wherein the vector comprises a bacmid and a reverse genetics competent unit of influenza virus. A method comprises wherein the vector comprises protein expression units and genome transcription units under the control of appropriate promoters. A method comprises wherein live attenuated influenza vaccine is produced directly in vivo. A method comprises providing the vector in a cell to the pig. A method comprises wherein a booster immunization of the vector is administered at least a second time to the pig. A method comprises wherein a booster immunization of a killed or attenuated vaccine of the influenza virus is administered at least a second time to the subject.

Influenza Virus Constructs

Disclosed are recombinant influenza viruses having a swine RNA polymerase I (pol I) sequence.

Swine RNA Polymerase I (pol I)

The present invention provides novel strategy for generating influenza viral-like RNAs. This strategy involves the transcription of negative-sense, viral RNA from a swine polymerase I promoter in swine cells. More specifically, the present invention comprises a strategy involving the use of the swine RNA polymerase I (pol I) promoter as a means to transcribe negative sense RNA species from cloned cDNA required for influenza viral RNA (vRNA) replication, transcription and related applications thereof. Because RNA polymerase I recognizes species-specific promoter sequences, this method is designed to work efficiently in porcine related cell types.

In order to replicate an RNA species, influenza polymerase requires an uncapped RNA of defined length with specific sequences at the five and three prime ends. Ribosomal RNAs are transcribed from the host genome by RNA polymerase I. This polymerase recognizes a promoter that is species-specific and initiates transcription of an uncapped RNA species at a defined start site. Transcription continues until the polymerase reaches the RNA polymerase I termination sequence at which transcription halts yielding an RNA species. Proper placement of the terminator sequence is necessary to define the termination site. Neumann et al. discovered that this system could be used to generate viral-like influenza RNA species and ultimately recombinant influenza viruses in human 293T cells with a human RNA polymerase I promoter (Neuman et al. Virology 202:477-479 (1994), Neuman et al. PNAS 96:9345-9350 (1999)). This system was further refined by introduction of the cloned cDNA into a bidirectional reverse genetic vector with the addition of an RNA polymerase II promoter to transcribe the mRNA of the same gene (Hoffman et al. Virology 267:310-317 (2000)). See FIG. 12. Although swine influenza viral DNA has been largely elucidated, the specific "start" and "stop" regions pertaining to the swine RNA polymerase I (pol I) promoter had not been identified until the findings of the present invention. The swine RNA polymerase I (pol I) promoter comprises GACCAGATG-GCTCTGAGAGCGCTGGGTCTGGC-GACTCTAGGGCAGGGCTGGGGG ACAAGTGTCCG-GATGGGGGTTCCGGGGATACCCCCACGTCCTGTGG-GTGGGCCC CGCTGCTGGGCATGGA-CATTTTTCGCGGCCGAAATACGCCTTTTCTGTCAC-CAGG TAGAT (SEQ ID NO: 1) The present invention further comprises a construct comprising SEQ ID NO: 1.

In certain embodiments, the swine RNA polymerase I (pol I) promoter sequence comprises a transcriptional start site downstream from the sequence provided by SEQ ID NO:1.

A cloning site for the insertion of cloned cDNAs (AGCGTCTTCatatgaattctattGAAGACGC) (SEQ ID NO:2). The present invention further comprises a reverse genetic vector comprising a CMV promoter, a murine polymerase I terminator sequence, a cloning site for genes to be transcribed, the swine polymerase I promoter sequence (SEQ ID NO:1), and a bovine growth hormone poly-adenylation signal.

In addition, the present invention may further comprise expression of cloned reporter or genes in the presence of influenza PB2, PB1, PA and NP proteins.

The present invention further comprises influenza virus from eight plasmid containing cloned cDNAs from the eight influenza segments transfected into porcine cell types.

Recombinant Proteins

The present invention comprises recombinant proteins comprising the swine RNA polymerase I (pol I) promoter encoded by SEQ ID NO:1.

In one aspect, the swine RNA polymerase I (pol I) promoter sequence comprises SEQ ID NO:1, and functional equivalents thereof. One of skill in the art can determine the effect of one or more substitutions on the functions of the polymerase.

Disclosed recombinant proteins comprising swine RNA polymerase I (pol I) promoter encoded by SEQ ID NO:1. may increase viral protein expression. An increase in viral protein expression can lead to an increase in virus production.

Constructs Containing NS1 and Exogenous Nucleic Acid Sequences

The swine influenza genome can be rearranged so that a foreign gene or an exogenous nucleic acid sequence of interest can be expressed downstream of the NS1 gene under the transcriptional control of the NS1 promoters. Because the NS1 gene is expressed very early during the viral life cycle and at high levels, exogenous nucleic acid sequences or foreign genes expressed co-translationally with the NS1 protein achieve high levels of expression in cells.

Disclosed constructs comprising swine RNA polymerase I (pol I) may comprise an NS1 nucleic acid sequence operably linked to an exogenous sequence. In one aspect, the NS1 nucleic acid sequence can be full length NS1. In one aspect, the NS1 nucleic acid sequence can be a partial NS1 gene sequence.

An exogenous sequence can be any nucleic acid sequence. In some aspects, an exogenous sequence can be an influenza nucleic acid sequence. An exogenous sequence can be an influenza sequence from a different or the same strain of influenza. For example, an exogenous sequence can be from an H5 strain and the NS1 sequence can be from an H9 strain.

An exogenous sequence may be an immune modulator for immunoprophylactic and therapeutic purposes. An immune modulator may be protective antigens derived from pathogenic organisms (viruses, bacteria, parasites, fungi and helminthes) or cancer cells. An exogenous sequence can be located downstream of an influenza gene, for example, the NS1 gene. Recombinant and wild-type genomic (not rearranged) segments may be used to produce recombinant influenza virus. For example, 6:2 virus reassortants can be made using 6 gene segments (PB2,PA,HA,NP,NA,M) from the strain of interest and 2 rearranged gene segments (PB1-NS2 and NS1-exogenous sequence). In like manner, 7:1 virus reassortants may be used, wherein in one genomic segment is rearranged and 7 genomic segments are wild-type. The present invention contemplates 7:1, 6:2, 5:3, 4:4 reassortants to produce recombinant influenza virus.

In some aspects, the exogenous sequence is a reporter gene. For example, a reporter gene such as enhanced green fluorescent protein (eGFP), turbo red fluorescent protein (TurboRFP), luciferase and others can be located downstream of an influenza gene, for example, the NS1 gene.

The presence of a reporter gene in the construct allows for production of recombinant virus expressing the reporter gene. The constructs or viruses can be used for studying influenza virus pathogenesis in vivo using bioluminescence imaging (BLI) or for studying influenza virus host-pathogen, influenza-bacteria and influenza-virus interaction in vivo.

Constructs Containing PB1 and NS2

An influenza genome may be rearranged wherein the NEP/NS2 protein may be expressed from a single open reading frame (ORF) downstream of the PB1 gene. Thus, a rearranged influenza viral genome segment may comprise a PB1 nucleic acid sequence operably linked to a NS2 nucleic acid sequence.

Packaging Signals

Disclosed constructs may comprise one or more influenza virus packaging signals. The packaging signals can be present at the 5' and/or 3' ends of the nucleic acid sequence that contains the rearranged viral genome.

A construct of the present invention may comprise one or more genomic segments wherein a genomic segment may comprise one or more of the following elements, including but not limited to, a wild-type influenza gene, a rearranged gene not found on that genomic segment in a wild-type influenza segment, a cleavage site, and one or more packaging signals.

Amplicons

Disclosed are amplicons comprising a termination sequence, an influenza nucleic acid sequence, and a promoter sequence. Wherein the termination sequence may comprise a t1 sequence or an influenza nucleic acid sequence. The influenza nucleic acid sequence of a disclosed amplicon can be any influenza nucleic acid sequence. In some aspects, the influenza nucleic acid sequence encodes one of the two major surface glycoproteins. For example, the influenza nucleic acid sequence can be a hemagglutinin nucleic acid sequence or a neuraminidase nucleic acid sequence. The promoter sequence included in a disclosed amplicon preferably comprises swine RNA polymerase I (pol I) promoter encoded by SEQ ID NO: 1.

Produced with Amplicons

Disclosed are recombinant influenza viruses produced by a method of transfecting cells with one or more of the disclosed amplicons. A recombinant virus can be produced using amplicons comprising one or more of the viral genes. For example, nucleic acid sequences of each of the eight viral genome segments can be provided using amplicons or a combination of amplicons and plasmids.

In some aspects, the recombinant influenza viruses can be produced by using one amplicon comprising the nucleic acid sequence of an influenza viral gene sequence, which is used in combination with the remaining seven genes required to produce influenza virus wherein those remaining seven genes may be present on plasmids used for reverse genetics. The present invention contemplates the use of one or more amplicons comprising the nucleic acid sequence of one or more influenza viral gene sequences to produce influenza virus. A plasmid-free method of producing influenza virus is disclosed herein.

Disclosed recombinant influenza viruses may be produced using one or more amplicons comprising an amplicon having an influenza gene sequence from an influenza strain that is a strain different from one or more source strains of the remaining influenza gene sequences. For example, plasmids containing 7 influenza viral genome segments from an H9 influenza strain can be combined with an amplicon containing an H5 influenza genome sequence from the remaining genome segment. For example, seven different amplicons, each containing one of 7 influenza viral genome segments from an H9 influenza strain can be combined with an amplicon containing an H5 influenza genome sequence from the remaining genome segment. The present invention contemplates combinations of one or more amplicons, each comprising an influenza genome segment sequence, a portion of an influenza genome segment, or a rearranged influenza genome segment comprising influenza genes and/ or exogenous sequences, with one or more amplicons comprising wild-type influenza genomic segment sequences from the same or a different strain of influenza. The present invention contemplates combinations of one or more amplicons, each comprising an influenza genome segment sequence, a portion of an influenza genome segment, or a rearranged influenza genome segment comprising influenza genes and/or exogenous sequences, with one or more amplicons comp an influenza genome segment sequence, a portion of an influenza genome segment, or a rearranged influenza genome segment comprising influenza genes and/ or exogenous sequences, from the same or a different strain of influenza.

Disclosed recombinant influenza viruses can be produced using one or more amplicons wherein each amplicon has at least one viral genome gene sequence.

Disclosed recombinant influenza viruses can be produced from a method comprising providing to an in vitro system a hemaggluttinin nucleic acid sequence present on an amplicon. In some aspects, the remaining seven nucleic acid gene sequences required to produce influenza virus can be neuraminidase, matrix, nucleocapsid, PB1, PB2, PA, NS1, and NS2.

Disclosed recombinant influenza viruses produced by methods comprising using at least one amplicon may comprise an amplicon that contains a rearranged viral genome segment or a mutated polymerase sequence. In some aspects, the methods used to produce virus comprise a plurality of amplicons comprising an amplicon comprising at least one rearranged genome segment and an amplicon comprising a mutated polymerase Influenza Vaccines Disclosed are vaccines comprising a recombinant influenza virus having a swine RNA polymerase I (pol I) promoter encoded by SEQ ID NO: 1. Vaccines of the present invention comprise live or killed virus, pharmaceutical compositions comprising virus, viral peptides, viral epitopes or combinations thereof, and may further comprise immunogenic compounds, stimulants or adjuvants.

The vaccines of the present invention may comprise other known pathogens including other influenza viruses, including but not limited to H5N1, H9N2 and H3N2 virus. Other pathogens or portions of pathogenic agents may need to be cloned into sites of the vector that are suitable for use in the vaccines, methods and compositions of the present invention.

Vaccines may be provided with an adjuvant. Adjuvants, such as but not limited to alum can be used with vaccines of the present invention.

Disclosed herein are methods of in vivo synthesis of a vaccine, comprising, providing to at least one cell of a subject at least one vector comprising an exogenous DNA construct encoding at least a portion of a pathogenic agent such as influenza virus, wherein one or more antigenic peptides encoded by the DNA construct are expressed in the cell and stimulate an immune response in the subject to the pathogenic agent. A method may comprise wherein one or more copies of at least a portion of a genome of a pathogenic agent are expressed in the cell. A method may comprise wherein the DNA construct is a reverse genetics competent unit. A method may comprise wherein multiple copies of a pathogenic agent genome are expressed in the cell. A method may comprise wherein the vector further comprises a reverse genetics competent unit. A method may comprise wherein the vector comprises a bacmid, a baculovirus expression system, or a synthetic vector. A method may comprise wherein the pathogenic agent comprises a virus, a bacteria or a parasite. A method may comprise wherein the pathogenic agent comprises an orthomyxovirus. A method may comprise wherein the pathogenic agent comprises an influenza virus. A method may comprise wherein the vector comprises a recombinant baculovirus vector and a reverse genetics competent unit comprising influenza virus. A method may comprise wherein the vector comprises a bacmid and a reverse genetics competent unit of influenza A virus. A method may comprise wherein the vector comprises protein expression units and genome transcription units under the control of appropriate promoters. A method may further comprising protein expression units under the control of RNA pol II promoters and viral transcription units under the control of RNA pol I promoters. A method may comprise wherein live attenuated influenza vaccine is produced directly in vivo. A method may comprise providing the vector in a cell to the subject. A method may comprise wherein two vectors are provided, and one vector encodes surface antigens of the pathogenic agent. A method may comprise wherein two vectors are provided, and one vector encodes proteins for replication of the pathogenic agent.

Methods of Immunizing or Inducing Protective Immunity

Disclosed are methods of immunizing or inducing a protective immune response in a subject against influenza virus by administering an effective amount of a recombinant influenza virus. A recombinant virus may comprise a swine RNA polymerase I (pol I) promoter encoded by SEQ ID NO:1.

In some aspects, administering a recombinant influenza virus includes administering a vaccine composition comprising a recombinant influenza virus. The vaccine composition may comprise a recombinant virus as well as other agents such as but not limited to adjuvants or stabilizers. In some aspects, administering a recombinant influenza virus includes administering a composition comprising the recombinant influenza virus. In some additional aspects, administering a recombinant influenza virus includes administering a composition comprising the recombinant influenza virus comprising a swine RNA polymerase I (pol I) promoter.

Methods of Increasing Viral Protein/Viral Particle Production

Disclosed are methods of increasing influenza viral protein production by administering to a subject an effective amount of a recombinant influenza virus comprising a vector and a swine RNA polymerase I (pol I) promoter encoded by SEQ ID NO:1. An effective amount can be an amount of recombinant virus that results in an increase of viral protein production compared to a wild-type virus. In certain embodiments the vector comprises bacmid, baculovirus expression system, and synthetic vectors.

In some aspects, administering a recombinant influenza virus includes administering a composition comprising the recombinant influenza virus. Active agents other than the recombinant influenza virus may be present in the composition. In some aspects, a recombinant influenza virus is the only active agent.

Disclosed are methods of increasing influenza viral particle production by transfecting cells with a construct that comprises a gene that encodes a recombinant protein, wherein the recombinant protein comprises a swine RNA polymerase I (pol I) promoter encoded by SEQ ID NO:1, optionally in combination with the gene sequences for hemagglutinin (HA), neuraminidase (NA), matrix (M1), nucleocapsid (NP), NS1 and NS2.

A construct that comprises the gene sequences can be a plasmid or an amplicon. The gene sequences for other influenza genes, including but not limited to, HA, NA, M1, NP, NS1 and NS2, may be provided on plasmids or amplicons.

Methods of Producing Amplicons

Disclosed are methods of producing an amplicon comprising the steps of a) amplifying a first fragment, wherein the first fragment comprises a fragment of a viral nucleic acid sequence and a termination sequence; b) ampliflying a second fragment, wherein the second fragment comprises a fragment of a viral nucleic acid sequence; c) amplifying a third fragment, wherein the third fragment comprises swine RNA polymerase I (pol I) promoter encoded by SEQ ID NO:1; and d) combining the three fragments to form an amplicon comprising a termination sequence, a viral nucleic acid sequence, and a promoter sequence. A termination sequence may be t1 signal sequence. Disclosed amplicons can be produced using these steps.

The fragment of a viral nucleic acid sequence in the first fragment and the viral nucleic acid sequence in the second fragment may comprise substantially all or a portion of the same nucleic acid sequence. In other words, the fragment of a viral nucleic acid sequence in the first fragment may comprise the same sequence as part of the nucleic acid sequence in the second fragment. For example, the first fragment and second fragment may comprise a viral nucleic acid sequence from the same viral gene or regulatory sequence.

In some aspects, the influenza nucleic acid sequence may comprise a hemagglutinin or neuraminidase nucleic acid sequence. The fragment of influenza nucleic acid sequence in the first fragment and the influenza nucleic acid sequence in the second fragment may comprise sequences from the same or a different (such as a different strain) hemagglutinin or neuraminidase gene sequence.

Disclosed methods comprise amplification of a first fragment, wherein the first fragment can be amplified using a forward primer and reverse primer, wherein the forward primer includes the termination sequence. The termination sequence in the amplicons may comprise a t1 signal sequence.

Disclosed methods of producing an amplicon may comprise a method of producing an amplicon that contains swine RNA polymerase I (pol I) promoter encoded by SEQ ID NO:1.

Methods of Producing a Recombinant Virus Using Amplicons

Disclosed are methods of producing a recombinant virus using amplicons. The amplicons can be produced by the methods disclosed herein. Both RNA and DNA viruses can be produced using methods disclosed herein comprising amplicons. Methods of producing recombinant virus using amplicons can provide a faster and more reliable method of producing virus.

It is known that viruses, such as but not limited to influenza, adenovirus, adeno-associated and lentivirus, can be made using multiple plasmids each containing different viral genes required to make the virus. Thus, for example, when a new strain of influenza evolves, the genes particular for that new strain, for example the HA or NA genes, have to be cloned into appropriate plasmid backbones so that influenza viral vaccines containing the new strain can be produced. The steps of cloning the mutated genes can be time-consuming and in some instances can be very difficult. The use of methods of the present invention comprising amplicons to produce recombinant virus provides an alternate method that can be quicker and easier to perform. Methods of reproducing virus are not limited to the viruses disclosed herein, but may be used for reproduction, in vitro, of any DNA or RNA genome virus.

Methods of producing recombinant virus comprising amplicons comprising providing in an in vitro system for viral reproduction one or more amplicons coding for at least one viral gene. An amplicon for use in such system may comprise an RNA polymerase signal, a termination signal and at least a portion of one viral gene or regulatory sequence. The methods can involve using a combination of amplicons and plasmids coding for the viral genes. The methods may comprise using only amplicons for carrying the viral genes. A method for producing a viruse comprises a) providing one or more amplicons, each of which comprises a gene or a portion of a gene of a virus to an in vitro cellular system comprising a polymerase capable of transcribing the amplicon viral genes and b) culturing the cells under circumstances that allow for virus production. The method can further comprise harvesting the virus from the cells or from the cell media. Those methods known in the art for producing viruses using plasmids can be used herein except for replacing the plasmids with the disclosed amplicons. Once the amplicons are in the cells, the remaining steps of producing the virus are the same as those known in the art for producing virus using plasmids.

Methods of Using a Recombinant Virus Expressing a Reporter Gene

Disclosed are methods for using one or more disclosed recombinant viruses expressing a reporter gene.

In some aspects, methods comprising recombinant influenza virus expressing a reporter gene may be useful for measuring or detecting influenza-specific neutralizing antibodies or for measuring or detection of replication of such an influenza virus in biological samples. For example, a reporter gene, such as a secreted luciferase gene (Gaussia luciferase-GLuc), can be positioned downstream of an influenza sequence, such as the NS1 gene, and under the regulatory control of the influenza gene or its regulatory sequences, and combinations of reassortants comprising wild-type and rearranged genome segments may be used to produce a recombinant virus or viral proteins. For example, 6:2 virus reassortants can be made comprising 6 wild type gene segments (PB2, PA, HA, NP, NA, M) from the strain of influenza of interest and 2 rearranged gene segments (PB1-NS2 and NS1-GLuc).

Disclosed are methods for studying influenza virus pathogenesis using in vivo bioluminescence imaging (BLI). A reporter gene can be positioned downstream of the NS1 gene and 6:2 virus reassortants are made using 6 wild type gene segments (PB2,PA,HA,NP,NA,M) from the strain of interest and 2 rearranged gene segments (PB1-NS2 and NS1-Luc).

Disclosed are methods for studying influenza virus host-pathogen, influenza-bacteria and influenza-virus interaction in vivo. A reporter gene such as enhanced green fluorescent protein (eGFP), turbo red fluorescent protein (TurboRFP) and other known reporter or label sequences can be positioned downstream of an influenza gene or regulatory sequences, such as the NS1 gene, and reassortants may be used to produce recombinant virus or viral proteins and nucleic acids. For example, 6:2 virus reassortants can be made using 6 wild type gene segments (PB2,PA,HA,NP,NA, M) from the strain of interest and 2 rearranged gene segments (PB1-NS2 and NS1-reporter). Interaction of influenza viruses expressing the reporter with host cells can be detected and quantified using known approaches such as microscopy, fluorescence activated cell sorting (FACS), and immunological techniques. Similarly, interaction of influenza virus expressing a reporter gene with either viral or bacterial pathogens expressing a different reporter gene can be detected and measured in vivo.

Disclosed are methods for high-throughput identification of host factors involved in influenza virus infection, for example, during multiple rounds of replication. A reporter gene, such as secreted luciferase gene (Gaussia luciferase-Gluc), may be positioned downstream of an influenza gene and/or regulatory sequences, for example, the NS1 gene and reassortants may be made. For example, 6:2 virus reassortants can be made using 6 wild type gene segments (PB2, PA,HA,NP,NA,M) from the influenza strain of interest along with 2 rearranged gene segments (PB1-NS2 and NS1-Gluc). Genome-wide RNA interference (RNAi) screens to identify host factors that are involved in or required for influenza virus replication can be easily detected using Gluc as the detected label.

Disclosed are methods for studying influenza virus co-infection and reassortament in in vitro, ex-vivo and in vivo systems. A suitable reporter gene may be positioned downstream of an influenza gene and/or regulatory sequences, for example, the NS1 gene and reassortants may be made. For example, 6:2 virus reassortants are made using 6 wild type gene segments (PB2,PA,HA,NP,NA,M) from the strain of interest and 2 rearranged gene segments (PB1-NS2 and NS1-reporter). Viruses expressing different reporter genes can be produced this way and studied in several biological systems. Alternatively, viruses expressing different domains of GFP can be used in co-infection experiments and intracellular assembly of the two GFP domains creates a molecular switch to detect infection of the same cell by different viruses.

Administration

Vaccines, compositions, constructs and viruses of the present invention disclosed herein can be for administration by oral, parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in unit dosage forms appropriate for each route of administration.

Administration to subjects usually involves the construct, virus or vaccine of interest to be formulated into a pharmaceutically acceptable carrier. Pharmaceutically acceptable carriers are well known in the art.

Administration of the disclosed compositions can be accomplished by any acceptable method which allows an effective amount of the recombinant influenza virus to achieve its intended effects. The particular mode selected will depend upon factors such as the particular formulation and the dosage required to induce an effective response.

Kits

Vaccines, compositions, constructs and viruses described herein as well as other materials can be packaged together in any suitable combination as a kit useful for performing, or aiding in the performance of, the disclosed method. It is useful if the kit components in a given kit are designed and adapted for use together in the disclosed method. For example disclosed are kits for producing amplicons, the kit comprising amplification primers. The kits also can contain nucleic acid sequences for some or all influenza genes, portions of sequences, and/or regulatory sequences.

DEFINITIONS

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a recombinant influenza virus" includes a plurality of such viruses, reference to "the nucleic acid sequence" is a reference to one or more nucleic acid sequences and equivalents thereof known to those skilled in the art, and so forth.

As used herein the term "effective amount" or means a dosage sufficient to provide the desired pharmacologic and/or physiologic effect. For example, an effective amount of a recombinant influenza virus can increase viral protein production, increase viral particle production, and increase a subject's immune response. The precise dosage will vary according to a variety of factors such as subject-dependent variables (e.g., age, immune system health, etc.).

The term "exogenous sequence" refers to a sequence other than a sequence found in the host. For example, a recombinant influenza virus with a rearranged genome that contains an exogenous sequence means that the exogenous sequence is a sequence other than a sequence found in the host influenza virus. The exogenous sequence can be from a different strain of influenza virus.

The term "operably linked" refers to nucleic acid sequences placed into a functional relationship with another nucleic acid sequence. For example, a promoter is operably linked to a coding sequence if it affects the transcription of the sequence. Generally, "operably linked" means that the nucleic acid sequences being linked are contiguous and in reading frame. With respect to a rearranged viral genome segment having NS1 operably linked to an exogenous sequence means that expression of the NS1 sequence results in expression of the exogenous sequence.

The term "rearranged viral genome" refers to a viral genome that has been altered or rearranged so that at least one nucleic acid sequence is in a different order from that of the wild type sequence. A rearranged viral genome can include one or more rearranged viral genome segments.

The term "subject" refers to a human or an animal, including a mammal, including, but not limited to, humans, dogs, cats, swine, ovine, bovine, rodents such as mice and rats, other laboratory animals, cells, and cell lines.

The terms "pig", "swine", "porcine" include all animals within the Sus genus, including but not limited to domesticated and wild pigs, boars, pot-bellied pigs, warthogs, babirus, red river hog, and bushog.

"Optional" or "optionally" means that the subsequently described event, circumstance, or material may or may not occur or be present, and that the description includes instances where the event, circumstance, or material occurs or is present and instances where it does not occur or is not present.

As used herein the term "modulate" is meant to mean to alter, by increasing or decreasing. For example, disclosed herein are methods of using vectors comprising an exogenous DNA construct to increase viral production.

Ranges can be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Those skilled in the art will recognize, or be able to ascertain using no more than routine experimentation, many equivalents to the specific embodiments of the method and compositions described herein. Such equivalents are intended to be encompassed by the following claims.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

EXAMPLES

Construction of Plasmids

Materials and Methods

The NS 3'UTR-porcine RNA polymerase I promoter construct was synthesized from Genscript (Piscataway, N.J.) with NotI and BstEII terminal sites for cloning. pPIG-GLuc (NS) was produced directly from pDP-GLuc(NS) by sub-cloning the synthetic construct into the NotI and BstEII sites, effectively replacing the human pol I promoter with the porcine pol I promoter. To make the generic reverse genetic vector pPIG2012, the vector portion of pPIG-GLuc(NS) was amplified with ATATCGTCTCGTCCCCCCCAACTTCG-GAGGTCG (SEQ ID NO:3) and TATTCGTCTCGATC-TACCTGGTGACAGAAAAGG (SEQ ID NO:4) and digested with BsmBI. A small double stranded oligonucleotide insert was generated by mixing /5Phos/GGGACGA-GACGATATGAATTCTATTCGTCTCG (SEQ ID NO:4) and /5Phos/AGATCGAGACGAATAGAAT-TCATATCGTCTCG (SEQ ID NO:5) together and incubating at 95° C. for 1 minute, followed by a slow cool down to room temperature. This was then ligated into the digested PCR-generated vector. Viral segments from A/turkey/OH/313053/2004 (H3N2) were amplified and cloned into pPIG2012 in essentially the same manner as described in Hoffmann et al. (PNAS 97:6108-6113 (2000)) with alternative reverse primers.

TABLE 1

Sequencing statistics of bacmid cloned influenza genes

| | PB2 | PB1 | PA | HA | NP | NA | M | NS |
|---|---|---|---|---|---|---|---|---|
| Coverage | 100% | 100% | 100% | 100% | 100% | 100% | 100% | 100% |
| Percent Identity[1] | 100% | 100% | 100% | 100% | 100% | 100% | 100% | 100% |
| Number of Reads | 7325 | 6941 | 6385 | 4904 | 5239 | 4459 | 3411 | 3007 |
| Average Depth[2] | 412 | 398 | 382 | 372 | 416 | 391 | 379 | 379 |

[1]Compared to sequence of pPIG2012 plasmids
[2]Depth of unique reads

To generate the pΔFast-P6 construct, gene cassettes comprising the pCMV promoter, mTerm, cloned DNA, porcine pol I promoter, and bovine growth hormone polyadenylation signal were amplified from the individual reverse genetic plasmids with CMV Fwd ([RS]TGCCAAGTACGC-CCCCTATTG) (SEQ ID NO:7) and BGH Rev ([RS]TGGC-CGATTCATTAATGCAGCTG) (SEQ ID NO:8) where [RS] represents one of the restriction enzymes used to clone into pΔFast (See FIG. 6).

Cells and Tissue Culture

MDCK and PK(15) cells were cultured in Dulbecco's modified Eagle medium (Sigma-Aldrich, St. Louis, Mo.) supplemented with 25 mM HEPES (Sigma-Aldrich), 2 mM glutamine (Sigma-Aldrich), 10 mM HEPES (Invitrogen, Grand Island, N.Y.), and 10% fetal bovine serum (FBS; Sigma-Aldrich) and were grown at 37° C. under 5% CO2. HEK 293T cells were cultured in Opti-MEM (Sigma-Aldrich) with 10% FBS and grown at 37° C. under 5% $CO_2$.

Virus Rescue

Transfections for virus rescue were performed in co-culture, either HEK293T/MDCK (4:1) or PK(15)/MDCK (4:1) as indicated. Cells were seeded in DMEM in the presence of serum 24 hours prior to transfection. Transfection mixtures were generally prepared with 1 µg DNA/plasmid/gene segment in OptiMEM and TransIT-LT1 (2 µL/µg DNA, Minis, Madison, Wis.) in a total volume of 200 µL, and incubated for 30 minutes. For example, 6 µg of DNA was transfected for a plasmid encoding 6 reverse genetic cassettes. Media would be exchanged for 1 mL OptiMEM supplemented with 1× Antibiotics/Antimycotics Solution (OptiMEM-AB, Sigma), and the transfection mixture would be added drop wise to each well. At 6 hours post transfection (hpt), the transfection mixture would be replaced with 1mL OptiMEM-AB. At 24 hpt, 2 mL of OptiMEM-AB supplemented with 3 µg TPCK-treated Trypsin (Worthington Biochemical, Lakewood, N.J.) would be added to each well of the transfection. Unless otherwise noted, all transfections were incubated at 37° C. under 5% $CO_2$.

Deep Sequencing of Bacmids

Bacmids encoding Ty04 were sequenced essentially as described in the manufacturer's protocol for Lib-L chemistry with minor exceptions. Briefly, 500 ng of bacmid DNA was nebulized to an upper fragment limit of ~1250 bp. Barcoded adapters were obtained from IDT for RL014 and RL015. These were prepared following Roche TCB No. 2010-010 to a working stock concentration of 50 µM/adapter. Following end repair of nebulized bacmids, adapters were ligated onto each fragment library. Samples were then size selected to a lower limit of ~500 bp on Ampure XP beads (Beckman Coulter, Sykesville, Md.). The quality of each library was determined using the FlashGel system (Lonza, Walkersville, Md.). Libraries were quantified based on the 6FAM label on each adapter, and diluted to $1 \times 10^7$ fragments/library. Finally, libraries were loaded into the emPCR reaction at a concentration of 3 fragments/bead. Following the sequencing run, reads were de novo aligned and reference mapped to expected sequences, and compared to known sequence for the bacmid and influenza reverse genetic inserts.

Isolation of Baculovirus DNA

Genomic DNA was isolated from baculovirus stocks using a modified TRIzol protocol. First, 250 µL of baculovirus stock was treated with 20 U DNaseI (NEB, Ipswich, Mass.) and incubated at 37° C. for 1 hr. Following digest, 750 µL of TRIzol reagent (Life Tech) was added to each sample, mixed, and incubated at RT for 5 minutes. Added to each sample was 150 µL of chloroform. Samples were shook vigorously for 15 seconds, incubated at RT for 3 minutes, and spun at 12,000×g for 30 minutes for phase separation.

The aqueous upper phase was discarded, and 350 µL of Back Extraction Buffer (4M guanidine thiocyanate, 50 mM sodium citrate, 1M tris base) was added to each sample and centrifuged again at 12,000×g for 30 minutes. The aqueous phase was removed to a new tube and precipitated with 250 µL isopropanol at 12,000×g for 15 minutes. The pellet was washed with 500 µL 70% ethanol and precipitated at 12,000×g for 15 minutes. Finally, the ethanol was removed and the pellet was allowed to air dry for 10 minutes before being eluted in 50 µL of EB.

Figure 1:
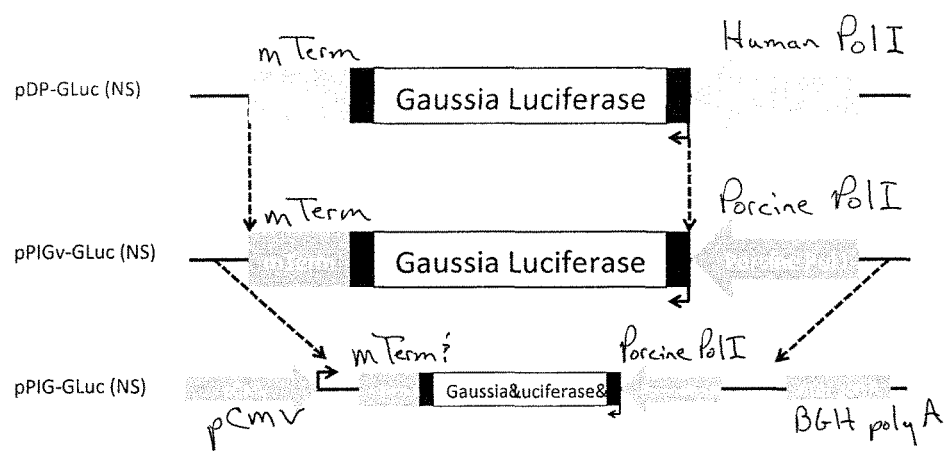
FIG. 1: Schematic representation of porcine pol I-based influenza reverse genetic system. The murine poll termination signal and a GLuc reporter, flanked by NS noncoding regions (black boxes), was subcloned from the human pol I vector pDP-GLuc (NS) and placed in front of the porcine pol I promoter to construct a viral RNA expression vector, pPIGv-GLuc (NS). This cassette was then subcloned between a RNA pol II promoter and bovine growth hormone polyadenylation signal to construct a bidirectional vector, pPIG-GLuc (NS).
Figure 2:
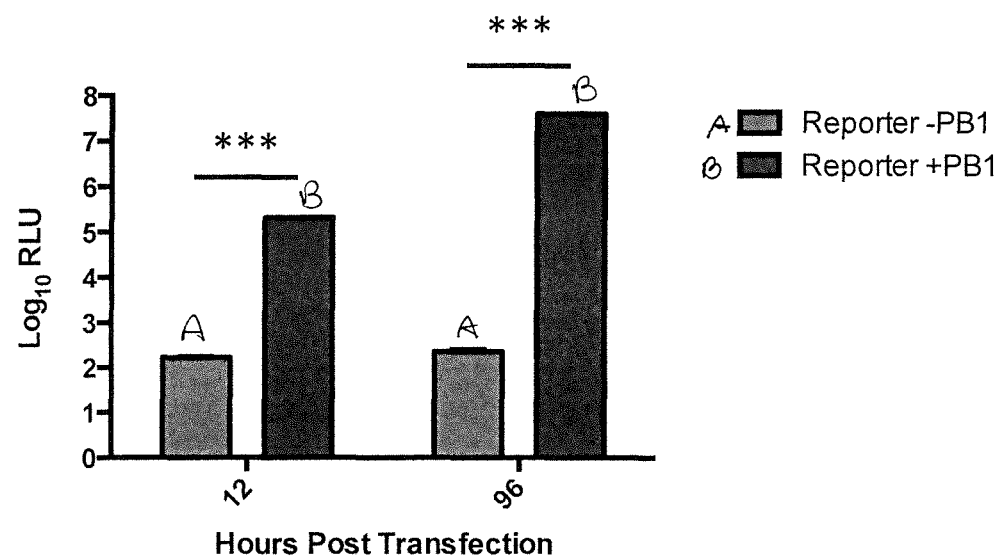
FIG. 2: IAV amplification of vRNA-like reporter gene expressed from porcine RNA pol I promoter. $1\times10^6$ PK(15)

Results: Construction of a Porcine pol I-Driven Uni- and Bidirectional Reverse Genetic Platform A secreted Gaussia luciferase (GLuc) reporter construct has previously been developed within our lab to assay IAV polymerase function in 293T cells (Journ Virol 85:456-469 (2011)). The vector is composed of a human pol I promoter that expresses a negative sense clone of a GLuc ORF that is flanked by segment 8 terminal noncoding regions. Transcription is terminated immediately thereafter by a murine RNA pol I termination sequence. The viral-like RNA that is produced is recognized by the IAV polymerase as an influenza segment. In order to test the ability of a porcine RNA pol I promoter to drive expression of a similar viral-like RNA species in swine cells, the human promoter from the GLuc report vector was replaced with the porcine RNA pol I promoter (FIG. 1). Porcine kidney cells (PK15) were then transfected with the porcine pol I IAV reporter plasmid along with RNA polymerase II expressed PB2, PA, and NP plasmids. As a control for IAV amplification, transfections were performed with or without the addition of a plasmid expressing PB1. As early as 12 hours post transfection (hpt), expression of the reporter gene was significantly greater in the presence of the full IAV polymerase compared to the negative control (FIG. 2). These results suggest a viral-like RNA was efficiently transcribed from the porcine pol I promoter, which was then recognized and amplified by the IAV polymerase. RNA polymerase I promoters have been reported to be species specific. Indeed, little sequence homology exists between the human promoter used in pHW2000-like vectors and the porcine promoter used in this study. To examine the species specificity of the porcine promoter in multiple cell types, GLuc expression of the human and porcine pol I reporter vectors was determined in their cognate and reciprocal cell types. Surprisingly, both the human and porcine pol I reporters functioned well in both 293T and PK(15) cells. As expected, however, the human pol I promoter and the porcine pol I promoter functioned significantly more efficiently in the human and swine derived cell types, respectively (FIG. 3). These results suggest that while a specific cell type may be preferred, an in vivo reverse genetic platform may be functional in more than the intended target.

Four proteins are sufficient and required to generate IAV from cloned cDNA; PB2, PB1, PA, and NP. The remainder of the genes need only to be expressed as vRNA in order for the polymerase complex to recognize, replicate, and perform mRNA transcription. Expression of these four proteins from "helper" plasmids in trans to replicate eight, co-transfected, pol I-derived, vRNA-like transcripts is common practice to generate IAV in tissue culture in a so called 12 plasmid (8 pol I+4 pol II) system. Alternatively, cloned cDNA can be inserted into bidirectional vectors expressing the negative sense or positive sense, vRNA or cRNA from a RNA pol I promoter and the mRNA from an RNA pol II promoter (Hoffman et al. PNAS 96:9345-9350 (1999)). This system requires that only eight plasmids be transfected in order to generate IAV de novo, and is the backbone of our rescue platform. To that end, the pCMV (RNA pol II) promoter and the bovine growth hormone polyadenylation signal (BGH polyA) were cloned upstream of the mTerm sequence and downstream of the porcine pol I cassette respectively to construct pPIG-GLuc (NS) (FIG. 1). Efficient expression of mRNA in eukaryotic cells requires the presence of both a 5' cap and a 3' polyadenylated tail. Proteins recognize both structures and each other through adapters to make a circular transcript that is read by the ribosome. The absence of either structure signals that the transcript may be regarded as foreign, and should be degraded by the cell. To determine if the mRNA expression cassette was functional, PK15 cells were transfected with the pol I reporter vector lacking a RNA pol II promoter, the reporter vector with the addition of the pCMV RNA pol II promoter, or the reporter vector containing both the pCMV promoter and the BGH polyA signal in the absence of the IAV polymerase. Expression of the reporter gene was increased by about 72-fold over the negative control in the presence of the CMV promoter, and by about 1000-fold with the addition of a polyadenylation signal (FIG. 4). These results strongly suggest that the GLuc reporter gene is being expressed in the cell via a cap dependent manner, and that the mRNA expression cassette on the plasmid is functioning properly.

An Eight Plasmid, Porcine pol I-Driven Rescue of Influenza A Virus in Tissue Culture Having generated a bidirectional, porcine pol I-driven reverse genetic vector, we wanted to determine if a full influenza virus could be rescued from this vector in tissue culture. A/turkey/OH/313053/2004 (Ty/04), a swine-origin, triple reassortant H3N2 virus, has been characterized and attenuated in our lab to server as a master vaccine backbone (Pena et al. Journ of Virol 85:456-469 (2011)). In addition to rescuing well from human pol I reverse genetic platforms, the wild type virus induces a febrile response, macro- and microscopic pneumonic lesions, and severe clinical signs in inoculated pigs, making it an ideal candidate as a proof of principle for the porcine pol I rescue system. To facilitate the insertion of cloned IAV cDNA into the vector, the flu-amplifiable GLuc reporter was replaced with BsmBI cloning sites similar to those used in the pHW2000 vector. Each of the eight segments from Ty/04 were cloned into this porcine pol I, influenza reverse-genetic vector, pPIG2012 (FIG. 5A). The full set of plasmids encoding Ty/04 were then transfected into PK15/MDCK co-culture to determine if this reverse genetic platform could in fact launch infectious virus in vitro. Following the addition of TPCK-treated trypsin at 24 hpt, a dramatic increase in viral replication was observed in transfected cells throughout 72 hpt (FIG. 5B).

Construction of a Baculovirus Vectored Porcine pol I-Driven Influenza Reverse Genetic Platform Baculoviruses have been used to provide a platform for the expression of foreign proteins in large quantities for many years. Commercially available kits provide a rapid way to insert genes of interest into baculoviruses for expression in insect cells. To make these recombinant bacmids, foreign genes were inserted into a donor vector under the transcriptional control of the polyhedron promoter. The expression cassette, located within a mini-Tn7 element, is then transposed into a bacmid encoding the mini-attTn7 attachment site with the aid of a helper plasmid. The bacmid, bMON14272, encodes the genome of Autographa californica nuclear polyhedrosis virus (AcNPV), and is capable of launching infectious virus in insect cells. AcNPV baculoviruses have also been shown to be powerful transducers of foreign genes into a wide range of mammalian cell types (Condreay et al. PNAS 96:127-132(1999)). This system was used with modification as the basis of a "Trojan horse" approach for the rescue of influenza virus in vivo.

The internal genes from Ty/04 were used as the backbone in this proof of principle. The virus rescues well in tissue culture, and causes mild to moderate disease signs in infected pigs, which may serve as disease signs for in vivo rescue. Additionally, the attenuated strain protects very well in homo- and heterologous challenge. To construct the backbone donor vector, reverse genetic cassettes from each individual pPIG2012 plasmid (PB2, PB1, PA, NP, M, and NS) were amplified from the start of the pCMV promoter to the end of the BGH polyA signal, and cloned into one of the restriction sites in the pΔFast donor vector (FIG. 6). As the donor vector became more and more unstable with the addition of more influenza cassettes, construction was done in two parts, cloning PB2, PB1 and PA in to one vector (pΔFast-P1), and NS, NP, and M into another (pΔFast-P2). The latter cassettes were then subcloned into the former vector as one large piece to generate a pΔFast-P6 (Ty04) donor vector containing the six internal genes of Ty04 (FIG. 6).

Although the individual reverse genetic plasmids are stable in bacteria, the addition of each gene cassette into pΔFast resulted in a higher occurrence of unstable clones. To confirm that each plasmid during the construction process was stable, each was tested for functionality. With the exception of M, the activity of the internal genes cloned into pΔFast can be assayed with a minireplicon system. Each pΔFast construct was transfected into PK(15) cells with the porcine Gaussia luciferase reporter, pPIG-GLuc(NS), and supplemented with individual plasmids required for influenza segment replication (PB2, PB1, PA or NP). For example, pΔFast-P1.2 contains reverse genetic cassettes for PB2 and PB1. The minireplicon was restored with the addition of pPIG-PA and pPIG-NP. Each construct was assayed for activity at 24 and 48 hours post transfection. In each case, constructs exhibited significant activity above the negative control, indicating that the encoded reverse genetic cassettes were functional. Additionally, when a construct containing the NS cassette was transfected into cells, the resultant luciferase activity increased significantly over the plasmids that lacked NS. This increase in activity in the presence of the NS plasmid suggests that amplification of the reporter gene is mediated by the viral polymerase, as NS1 has been shown to stimulate viral mRNA gene expression at the detriment to host cell messages (Nemeroff et al. Molecular cell 1:991-1000(1998)).

In order to generate a plasmid encoding the six internal genes of Ty04, the fragment encoding the NS, M, and NP cassettes was subcloned into pΔFast-P1.3. This plasmid was termed pΔFast-P6, and contains the reverse genetic cassettes required for the expression of the backbone segment mRNAs and vRNAs. To test for the proper expression of internal genes, this construct was transfected into PK(15) cells along with the flu amplifiable GLuc reporter. After 24 hours post transfection, the polymerase expressed of the pΔFast-P6 promoter expressed GLuc to comparable levels compared to those produced by the transfection of six pPIG reverse genetic plasmids encoding the same genes (FIG. 7A). The same experiment was performed in which PK(15)/MDCK co-cultures were transfected with the pΔFast-P6 plasmid, supplemented with pPIG plasmids encoding HA and NA to test for virus rescue. As expected, virus was rescued at comparable levels to the positive control in which cells had been transfected with eight individual reverse genetic, pPIG plasmids (FIG. 7B). This data suggests that the internal genes from Ty04, cloned into the baculovirus entry vector, functionally produce mRNA and vRNA for each gene from a single plasmid.

The majority of vaccines currently produced use only the HA and NA of the circulating strain, and the internal genes generally come from a master donor strain. For human influenza vaccines, these strains are either A/PuertoRico/8/1934 (H1N1) for the inactivated vaccines, or A/AnnArbor/6/60 (H2N2) for the live-attenuated vaccines. To enable the rapid exchange of surface antigens in the baculovirus system, the pΔFast-P6 plasmid was further modified by the insertion of a constitutively expressed thymidine kinase gene flanked by lambda phage attR1 and attR2 sites (pΔFast-P6Tkatt, ~19.6 kbp), enabling this vector to be compatible with the Gateway cloning system. The HA and NA reverse genetic cassettes from Ty04 were subcloned into pENTR-1A in a similar manner as the remaining genes into pΔFast (FIG. 6). The complete reverse genetic system containing all eight genes for Ty04 was subsequently generated through recombination of the pENTR-HANA Gateway cassette into pΔFast-P6TKatt. This pΔFast-P8 plasmid was about 26 kbp in size, and efficiently rescued influenza virus after transfection into PK(15) cells (FIG. 9).

The Bac-to-bac baculovirus system offers a convenient method of generating recombinant baculoviruses quickly from inserts cloned into the pFastBac vector and its derivatives, such as pΔFast. The system is based on the bMON14272 baculovirus shuttle vector, which encodes a modified AcMNPV genome containing a mini-F replicon and an attachment site for the Tn7 transposon (25). To generate the recombinant bacmid encoding the complete reverse genetic system for Ty04, pΔFast-P8 (Ty04) was transfected into DH10Bac, which contained the shuttle vector together with the components required for Tn7 integration. Bacmids containing the Tn7 insert from pFast-P8 (Ty04) were selected for on kanamycin and gentamycin LB agar plates. PCR of the bacmid indicates that each influenza gene from Ty04 is present in the transposed bacmid (FIG. 8). To determine the stability of the viral sequence, 454 libraries were prepared from the bacmid, and the influenza gene inserts were sequenced in their entirety. Each gene was found to be present in the bacmid by sequencing, and no high confidence mutations were observed to have been introduced between the initial pPIG2012 vectors and the final bacmid (Table 1). Additionally, no deletions were observed to have occurred suggesting that the final bacmid product is stable despite the highly repetitive promoter regions of the reverse genetic cassettes.

Bacmid DNA (Bcmd-F1uRG) was transfected into mammalian tissue co-culture to determine whether the reverse genetic cassettes were functional for virus rescue. The DNA copy numbers of the bacmid and the pΔFast-P8 plasmid were normalized to that of pPIG-PB2 (Ty04), which contains $1.76 \times 10^{11}$ copies/μg. This corresponded to 31.5 μg and 4.94 μg of the bacmid and pΔFast-P8 plasmid DNA, respectively. Supernatant from each transfection was titrated every 24 hours for 3 days. Although the bacmid DNA was delayed in its amplification, virus titers in the supernatant recovered to similar levels as the controls by 3 days post transfection (FIG. 9). It should also be noted that the bacmid transfection was hindered by DNA precipitation and a high toxicity due to the amount of transfection reagent used. Regardless, the bacmid encoding Ty04 reverse genetic cassettes is competent for the rescue of influenza in tissue culture.

Rescue of influenza virus from eight plasmid systems is efficient, and has become routine in many labs. DNA in the transfection generally reaches $10^5$ copies of each plasmid per cell. This ensures that cells receive, on average, many copies of each plasmid in the eight-plasmid set. As a single bacmid contains the complete complement of gene cassettes required to rescue influenza virus, we reasoned that transfection of the bacmid and subsequent virus rescue would be more efficient than the standard eight-plasmid transfection scheme. To do this, transfections were performed as before, but $2.8 \times 10^{10}$ copies of either the bacmid DNA or each of the eight pPIG2012 plasmids encoding Ty04. This represents a 6.4× reduction in the amount of DNA previously used, and is about the limit at which virus can be consistently rescued from the bacmid. For the bacmid, this transfection consists of 5 μg total DNA while the individual plasmids range from 159 ng (pPIG-PB2) to 115 ng (pPIG-NS) depending on the length of the influenza gene insert. Similar peak titers were observed for both the bacmid transfection and the pPIG2012 transfection. Although the difference was not significant, the bacmid tended to grow to higher titers than the eight-plasmid transfection (FIG. 10). Rescue of the bacmid was also more consistent with the bacmid with 3/3 replicates rescuing virus compared to the eight-plasmid transfection, which only had 2/3 replicates rescue. These results may suggest that while the bacmid contributes a complete reverse genetic, any gain in efficiency may be modulated by other factors such as transfection efficiency or nuclear transport of such a large DNA molecule.

Bcmd-F1uRG also contains the information required to rescue AcNPV baculovirus in insect cell culture. This allows for an additional mode of reverse genetic competent DNA entry into target cells as baculoviruses have been shown to be strong transducers of mammalian cell types (Condreay et al. PNAS 96: 127-132 (1999)). To determine if the Bcmd-F1uRG DNA could indeed generate baculovirus, bacmid DNA was transfected into Sf9 insect cells. At 96 hours post transfection, the supernatant was collected, clarified with low speed centrifugation, and treated with DNaseI to remove any contaminating bacmid DNA from the transfection. DNA protected within virions was then purified, and each of the eight influenza genes encoded within the baculovirus genome was amplified with full-length primers (FIG. 11A). The transfected cells were also fixed and stained for gp64, a baculovirus surface glycoprotein (FIG. 11B). Baculovirus was passaged 4 subsequent times, and DNA prepared as before. Again, PCR amplification indicates the presence of all eight influenza reverse genetic cassettes within the genome of the baculvirus (FIG. 11A). Together, these data indicate that the Bcmd-F1uRG bacmid is competent for the rescue of baculovirus containing the reverse genetic cassettes required for the rescue of influenza virus, and that these cassettes are stable over multiple passages.

Discussion

Vaccines must be produced quickly and reliably without changing the antigenicity of the seed strain. Although the advent of reverse-genetics for influenza virus has enabled vaccines to be produced much more quickly, seed stocks must ultimately be propagated in traditional substrates such as tissue culture or embryonated eggs. Vaccine candidate viruses also may not be well adapted for growth in these non-natural substrates, as was the case for the 2009 human H1N1 vaccine, and adapting for high growth strains may adversely affect the intended antigenicity of the vaccine stock. Next generation vaccines must be able to be produced rapidly, in high yields, and with high antigenic fidelity to the circulating strains. The present invention provides a DNA or a baculovirus-based vaccine for the production of influenza viruses in swine cells with the intent of producing an in vivo reverse genetic vaccine. Cloned cDNA from a triple reassortant swine virus, Ty04, was introduced into a reverse genetic vector and transcribed into a viral-like RNA species under the control of a porcine RNA polymerase I promoter. The reverse genetic cassettes for each of the eight segments, consisting of the RNA polymerase II promoter, the cloned cDNA segment, the porcine RNA polymerase I promoter, and the bovine growth hormone polyadenylation signal, were serially cloned into a single shuttle vector and transposed into a bacmid encoding the AcNPV genome. The present invention demonstrateds that this bacmid is capable of rescuing both influenza and baculovirus in mammalian and insect cell culture, respectively.

Although single plasmid rescue strategies have been described previously it is known that these large plasmids with repetitive promoter sequences are unstable in $E.$ $coli$, and the cassettes are often lost. Bacterial artificial chromosomes (BACs), such as bMON14272 used here, are based off of the F factor and are maintained at low copy numbers thus increasing the stability of the DNA. The present invention enables rapid exchange of surface antigens by using the Gateway cloning system, and doesn't require ligations into large vectors. Given the higher cloning capacity of the BAC compared to traditional plasmids, the present invention enables the introduction of additional genes to act as immune modulators, increasing the response to the rescued virus. In summary, the present invention provides a reverse genetic system tailored to the rescue of influenza virus in swine cells with the potential to act as DNA or baculovirus based vectors for in vivo virus rescue and vaccination.

What is claimed is:

1. A method for generating recombinant influenza viruses in swine cells comprising administering to a swine cell a genetic construct comprising the sequences that encode a swine RNA polymerase I promoter, and at least one of a sequence encoding hemagglutinin, neuraminidase, matrix, nucleocapsid, PB1, PB2, PA, NS1 or NS2 in combination with one or more genetic constructs comprising the remaining viral genes, wherein the swine RNA polymerase I promoter sequence consists of SEQ ID NO: 1.

2. The method of claim 1, wherein the construct comprises a reverse genetics vector capable of being transcribed into a viral-like RNA species, wherein the reverse genetics vector comprises genetic cassettes for RNA polymerase II promoter, a cloned cDNA segment, porcine RNA polymerase I promoter, and bovine growth hormone polyadenylation signal.

3. The method of claim 2, wherein the RNA polymerase II promoter comprises a CMV promoter.

4. The method of claim 2, wherein the reverse genetics vector further comprises a murine polymerase I terminator sequence.

5. A genetic construct comprising a sequence encoding swine RNA polymerase I promoter and at least one of a swine influenza sequence encoding hemagglutinin, neuraminidase, matrix, nucleocapsid, PB1, PB2, PA, NS1 or NS2, wherein the swine RNA polymerase I promoter sequence consists of SEQ ID NO:1.

6. The construct of claim 5, wherein the construct comprises a reverse genetics vector capable of being transcribed into a viral-like RNA species, wherein the reverse genetics vector comprises genetic cassettes for RNA polymerase II promoter, a cloned cDNA segment, porcine RNA polymerase I promoter, and bovine growth hormone polyadenylation signal.

7. The construct of claim 6, wherein the RNA polymerase II promoter comprises a CMV promoter.

8. The construct of claim 6, wherein the reverse genetics vector further comprises a murine polymerase I terminator sequence.

9. The construct of claim 6, comprised in a pharmaceutical carrier.

10. A method of in vivo synthesis of a swine influenza immunogenic composition comprising providing, to at least one cell of a swine, a vector comprising an exogenous DNA construct comprising a swine RNA polymerase I promoter and a sequence encoding a swine RNA polymerase I, and at least one of a sequence encoding hemagglutinin, neuraminidase, matrix, nucleocapsid, PB1, PB2, PA, NS1 or NS2 thereby stimulating an immune response to swine influenza virus.

11. The method of claim 10, wherein the DNA construct is a reverse genetics competent unit.

12. The method of claim 10, wherein the vector further comprises a reverse genetics competent unit.

13. The method of claim 10, wherein the vector comprises a bacmid, a baculovirus expression system, or a synthetic vector.

14. The method of claim 10, wherein the vector comprises a recombinant baculovirus vector and a reverse genetics competent unit comprising influenza virus.

15. The method of claim 10, wherein the vector comprises a bacmid and a reverse genetics competent unit of influenza A virus.

16. The method of claim 10, wherein the vector comprises protein expression units and genome transcription units under the control of appropriate promoters.

17. The method of claim 10, wherein two vectors are provided, and at least one vector encodes surface antigens of the influenza virus or encodes proteins used in replication of the influenza virus.

* * * * *

SEQUENCE LISTING

<160> NUMBER OF SEQ ID NOS: 8

<210> SEQ ID NO 1
<211> LENGTH: 168
<212> TYPE: DNA
<213> ORGANISM: Artificial Sequence
<220> FEATURE:
<223> OTHER INFORMATION: synthetic construct; swine polyermase I
      promoter sequence

<400> SEQUENCE: 1
gaccagatgg ctctgagagc gctgggtctg gcgactctag ggcagggctg ggggacaagt    60
gtccggatgg gggttccggg gatacccca cgtcctgtgg gtgggcccg ctgctgggca    120 tggacatttt tcgcggccga aatacgcctt ttctgtcacc aggtagat              168

-continued

<210> SEQ ID NO 2
<211> LENGTH: 31
<212> TYPE: DNA
<213> ORGANISM: Artificial Sequence
<220> FEATURE:
<223> OTHER INFORMATION: synthetic construct; cloning site

<400> SEQUENCE: 2
agcgtcttca tatgaattct attgaagacg c                                    31

<210> SEQ ID NO 3
<211> LENGTH: 33
<212> TYPE: DNA
<213> ORGANISM: Artificial Sequence
<220> FEATURE:
<223> OTHER INFORMATION: synthetic construct; primer

<400> SEQUENCE: 3
atatcgtctc gtcccccca acttcggagg tcg                                   33

<210> SEQ ID NO 4
<211> LENGTH: 33
<212> TYPE: DNA
<213> ORGANISM: Artificial Sequence
<220> FEATURE:
<223> OTHER INFORMATION: synthetic construct; primer

<400> SEQUENCE: 4
tattcgtctc gatctacctg gtgacagaaa agg                                  33

<210> SEQ ID NO 5
<211> LENGTH: 32
<212> TYPE: DNA
<213> ORGANISM: Artificial Sequence
<220> FEATURE:
<223> OTHER INFORMATION: synthetic construct; oligonucleotide

<400> SEQUENCE: 5
gggacgagac gatatgaatt ctattcgtct cg                                   32

<210> SEQ ID NO 6
<211> LENGTH: 32
<212> TYPE: DNA
<213> ORGANISM: Artificial Sequence
<220> FEATURE:
<223> OTHER INFORMATION: synthetic construct; oligonucleotide

<400> SEQUENCE: 6
agatcgagac gaatagaatt catatcgtct cg                                   32

<210> SEQ ID NO 7
<211> LENGTH: 21
<212> TYPE: DNA
<213> ORGANISM: Artificial Sequence
<220> FEATURE:
<223> OTHER INFORMATION: synthetic construct; primer

<400> SEQUENCE: 7
tgccaagtac gccccctatt g                                               21

<210> SEQ ID NO 8
<211> LENGTH: 23
<212> TYPE: DNA
<213> ORGANISM: Artificial Sequence
<220> FEATURE:
<223> OTHER INFORMATION: synthetic construct; primer

```
<400> SEQUENCE: 8
tggccgattc attaatgcag ctg                                              23
```